(12) United States Patent
Adam et al.

(10) Patent No.: US 10,377,828 B2
(45) Date of Patent: Aug. 13, 2019

(54) COMBINATION THERAPY FOR NEOPLASIA TREATMENT

(71) Applicant: Boehringer Ingelheim International GmbH, Ingelheim am Rhein (DE)

(72) Inventors: Paul Adam, Vienna (AT); Katrin Friedbichler, Vienna (AT)

(73) Assignee: Boehringer Ingelheim International GmbH, Ingelheim am Rhein ( * ) Notice: Subject to any disclaimer, the term of this patent is extended or adjusted under 35 U.S.C. 154(b) by 0 days.

(21) Appl. No.: 14/946,067

(22) Filed: Nov. 19, 2015

(65) Prior Publication Data

US 2016/0199488 A1     Jul. 14, 2016

Related U.S. Application Data

(62) Division of application No. 14/196,231, filed on Mar. 4, 2014, now abandoned.

(30) Foreign Application Priority Data

Mar. 7, 2013   (EP) ................................ 13518228.0

(51) Int. Cl.
| | | |
|---|---|---|
| *A61K 31/00* | (2006.01) | |
| *A61K 39/00* | (2006.01) | |
| *A61K 45/06* | (2006.01) | |
| *C07K 16/22* | (2006.01) | |
| *C07K 16/28* | (2006.01) | |
| *A61K 39/395* | (2006.01) | |
| *A61K 31/4164* | (2006.01) | |
| *A61K 31/4166* | (2006.01) | |

(52) U.S. Cl.
CPC .......... *C07K 16/2863* (2013.01); *A61K 31/00* (2013.01); *A61K 31/4164* (2013.01); *A61K 31/4166* (2013.01); *A61K 39/3955* (2013.01); *A61K 39/39558* (2013.01); *A61K 45/06* (2013.01); *C07K 16/22* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,342,566 A | 8/1982 | Theofilopoulos et al. | |
| 6,342,221 B1 | 1/2002 | Thorpe et al. | |
| 6,696,245 B2 | 2/2004 | Winter et al. | |
| 6,991,790 B1 | 1/2006 | Lam et al. | |
| 7,020,563 B1 | 3/2006 | Bentley et al. | |
| 7,037,498 B2 | 5/2006 | Cohen et al. | |
| 7,060,268 B2 | 6/2006 | Andya et al. | |
| 7,438,911 B2 | 10/2008 | Shitara et al. | |
| 7,498,415 B2 | 3/2009 | Shitara et al. | |
| 7,749,966 B2 | 7/2010 | Raso | |
| 7,910,098 B2 * | 3/2011 | Fuh ....... | C07K 16/005 424/130.1 |
| 8,318,159 B2 | 11/2012 | Adam et al. | |
| 8,580,254 B2 | 11/2013 | Adam et al. | |
| 2003/0138430 A1 | 7/2003 | Stimmel et al. | |
| 2004/0086503 A1 | 5/2004 | Cohen et al. | |
| 2006/0165695 A1 | 7/2006 | Shitara et al. | |
| 2007/0196376 A1 | 8/2007 | Raeber et al. | |
| 2009/0016967 A1 | 1/2009 | Schnapp et al. | |
| 2010/0099147 A1 | 4/2010 | Hariharan et al. | |
| 2010/0150940 A1 | 6/2010 | Adam et al. | |
| 2010/0196395 A1 | 8/2010 | Adam et al. | |
| 2013/0230541 A1 | 9/2013 | Adam et al. | |
| 2014/0199236 A1 * | 7/2014 | Chen .................. | A61K 9/0053 424/1.49 |
| 2014/0255413 A1 | 9/2014 | Adam et al. | |
| 2015/0010574 A1 | 1/2015 | Adam et al. | |
| 2015/0209426 A1 | 7/2015 | Bogenrieder et al. | |
| 2016/0199488 A1 | 7/2016 | Adam et al. | |
| 2017/0088609 A1 | 3/2017 | Solca et al. | |

FOREIGN PATENT DOCUMENTS

| | | |
|---|---|---|
| CA | 2473039 A1 | 7/2003 |
| CA | 2483848 A1 | 11/2003 |
| CA | 2536288 A1 | 3/2005 |
| CA | 2540133 A1 | 3/2005 |
| CA | 2540138 A1 | 3/2005 |
| EP | 0123228 A2 | 10/1984 |
| EP | 0292656 A1 | 11/1988 |

(Continued)

OTHER PUBLICATIONS

Liu et al., Neutralization of IGF-I and -II ligands with the fully humanized bispecific monoclonal antibody xentuzumab ,,, [abstract] In: Proceedings of the American Association for Cancer Research Annual Meeting 2017; Apr. 1-5, 2017; Washington, DC. Philadelphia (PA): AACR; Cancer Res 2017;77(13 Suppl):Abstract nr 1194. doi:10.1158/1538-7445.AM2017-.*
Pandini, Giuseppe, et al.; "Insulin/Insulin-like Growth Factor I Hybrid Receptors Have Different Biological Characteristics Depending on the Insulin Receptor Isoform Involved"; The Journal of Biological Chemistry; (2002) V. 277, Issue: 42, pp. 39684-39695.
Pollak, M.N., et al; Pharmacodynamic Properties of the Anti-IGF-IR Monoclonal Antibody CP-751,871 in Cancer Patients; American Society of Clinical Oncology (2007) vol. 25, No. 18S p. 3587.
Pollak, Michael N. et al.; "Insulin-Like Growth Factors and Neoplasia" Nature Reviews Cancer, (2004) vol. 4, pp. 505-518.

(Continued)

*Primary Examiner* — Marianne P Allen
(74) *Attorney, Agent, or Firm* — Edouard G. Lebel

(57) ABSTRACT

The present invention relates to an insulin-like growth factor (IGF) receptor antagonist for use in the treatment of prostate neoplasia, including benign prostatic hyperplasia (BPH), prostate cancer, and particularly CRPC, wherein the antagonist is used in combination with an androgen receptor antagonist. An embodiment of the invention is where the androgen receptor antagonist is enzalutamide.

2 Claims, 27 Drawing Sheets

Specification includes a Sequence Listing.

(56) References Cited

FOREIGN PATENT DOCUMENTS

| | | |
|---|---|---|
| EP | 0492552 A1 | 7/1992 |
| EP | 0700994 A1 | 3/1996 |
| EP | 1505075 A1 | 2/2005 |
| JP | 2003310275 A | 11/2003 |
| WO | 8500831 A1 | 2/1985 |
| WO | 1989011297 A1 | 11/1989 |
| WO | 9000562 A1 | 1/1990 |
| WO | 199429348 A2 | 12/1994 |
| WO | 9525794 A1 | 9/1995 |
| WO | 9928347 A1 | 6/1999 |
| WO | 02053596 A2 | 7/2002 |
| WO | 2002056910 A1 | 7/2002 |
| WO | 2003002609 A2 | 1/2003 |
| WO | 2003050531 A2 | 6/2003 |
| WO | 03059951 A2 | 7/2003 |
| WO | 03093317 A1 | 11/2003 |
| WO | 03100008 A2 | 12/2003 |
| WO | 03106621 A2 | 12/2003 |
| WO | 2004003019 A2 | 1/2004 |
| WO | 2004058821 A2 | 7/2004 |
| WO | 2004071529 A2 | 8/2004 |
| WO | 2004083248 A1 | 9/2004 |
| WO | 2005005635 A2 | 1/2005 |
| WO | 2005016970 A2 | 2/2005 |
| WO | 2005018671 A1 | 3/2005 |
| WO | 2005027970 A1 | 3/2005 |
| WO | 2005028515 A1 | 3/2005 |
| WO | 2005058967 A2 | 6/2005 |
| WO | 2005061541 A1 | 7/2005 |
| WO | 2006069202 A2 | 6/2006 |
| WO | 2006125640 A2 | 11/2006 |
| WO | 2007012614 A2 | 2/2007 |
| WO | 2007042309 A2 | 4/2007 |
| WO | 2007070432 A2 | 6/2007 |
| WO | 2007092453 A2 | 8/2007 |
| WO | 2007115814 A2 | 10/2007 |
| WO | 2007118214 A2 | 10/2007 |
| WO | 2007126876 A2 | 11/2007 |
| WO | 2007141626 A1 | 12/2007 |
| WO | 2008005469 A2 | 1/2008 |
| WO | 2008079324 A1 | 7/2008 |
| WO | 2008079849 A2 | 7/2008 |
| WO | 2008098917 A2 | 8/2008 |
| WO | 2008108986 A2 | 9/2008 |
| WO | 2008115470 A2 | 9/2008 |
| WO | 2008116103 A2 | 9/2008 |
| WO | 2008144345 A2 | 11/2008 |
| WO | 2008144720 A2 | 11/2008 |
| WO | 2008152422 A2 | 12/2008 |
| WO | 2008155387 A2 | 12/2008 |
| WO | 2009005673 A1 | 1/2009 |
| WO | 2009006336 A1 | 1/2009 |
| WO | 2009016164 A1 | 2/2009 |
| WO | 2009017679 A2 | 2/2009 |
| WO | 2009019117 A1 | 2/2009 |
| WO | 2009021054 A2 | 2/2009 |
| WO | 2009032145 A1 | 3/2009 |
| WO | 2009032782 A2 | 3/2009 |
| WO | 2009039457 A1 | 3/2009 |
| WO | 2009045361 A2 | 4/2009 |
| WO | 2009045389 A2 | 4/2009 |
| WO | 2009079587 A2 | 6/2009 |
| WO | 2009120767 A1 | 10/2009 |
| WO | 2009126304 A1 | 10/2009 |
| WO | 2009137378 A2 | 11/2009 |
| WO | 2009137758 A2 | 11/2009 |
| WO | 2009149185 A2 | 12/2009 |
| WO | 2010034441 A1 | 4/2010 |
| WO | 2010036767 A1 | 4/2010 |
| WO | 2010045315 A1 | 4/2010 |
| WO | 2010048123 A2 | 4/2010 |
| WO | 2010052344 A2 | 5/2010 |
| WO | 2010062896 A1 | 6/2010 |
| WO | 2010069858 A1 | 6/2010 |
| WO | 2010075511 A1 | 7/2010 |
| WO | 2010120592 A1 | 10/2010 |
| WO | 2011057064 A1 | 5/2011 |
| WO | WO 2010/066868 | * 6/2013 |
| WO | WO 2013/148 | * 10/2013 |
| WO | 2013169611 A1 | 11/2013 |

OTHER PUBLICATIONS

Quinn, Kathryn A., et al; insulin-Like Growth Factor Expression in Human Cancer Cell Lines; The Journal of Biological Chemistry (1996) vol. 271, No. 19 pp. 11477-11483.

Rauchenberger, Robert, et al; Human Combinatorial Fab Library Yielding Specific and Functional Antibodies Against the Human Fibroblast Growth Factor Receptor 3*; The Journal of Biological Chemistry (2003) vol. 278, No. 40 pp. 38194-38205.

Reinberg, Steven "Rare Gene Mutation Plays Role in Longevity" Healthday News, published by US News & World Report, Mar. 4, 2008; pp. 1-3.

Renehan, Andrew, G., et al; Circulating Insulin-Like Growth Factor II and Colorectal Adenomas; the Journal of clinical Endocrinology and Metabolism (2000) vol. 85, No. 9 pp. 3402-3408.

Renehan, Andrew, G., et al; Elevated Serum Insulin-Like Growth Factor (IGF)-II and IGF Binding Protein-2 in Patients with Colorectal Cancer; British Journal of Cancer (2000) vol. 83, No. 10 pp. 1344-1350.

Revets, Hilde, et al; Nanobodies as Novel Agents for Cancer Therapy; Experts Opin. Biol. Ther. (2005) vol. 5, No. 1 pp. 111-124.

Rubin, Raphael, et al; Biology of Disease: Insulin-Like Growth Factor-I Receptor; Laboratory Investigation (1995) vol. 73, No. 3 pp. 311-331.

Rudikoff, Stuart et al. "Single Amino Acid Substitution Altering Antigen-Binding Specificity" Proc. Natl. Acad. Sci. USA (1982) vol. 79, pp. 1979-1983.

Rusell, William, E., et al; Inhibition of the Mitogenic Effects of Plasma by a Monoclonal Antibody to Somatomedin C; Proc. Natl. Acad. Sci. USA (1984) vol. 81 pp. 2389-2392.

Schier, Robert, et al; Identification of Functional and Structural Amino-Acid residues by Parsimonious Mutagenesis; Gene (1996) vol. 169 pp. 147-155.

Scotlandi, Katia, et al; Insulin-like Growth Factor I Receptor-Mediated Circuit in Ewing's Sarcoma/Peripheral Neuroectodermal Tumor: A Possible Therapeutic Target; Cancer Research (1996) vol. 56 pp. 4570-4574.

Sell, Christian, et al; Effect of a Null Mutation of the Insulin-Like Growth Factor I Receptor Gene on Growth and Transformation of Mouse Embryo Fibroblasts; Molecular and Cellular Biology (1994) vol. 14, No. 6 pp. 3604-3612.

Sell, Christian, et al; Simian Virus 40 Large Tumor Antigen is Unable to Transform Mouse Embryonic Fibroblasts lacking Type 1 Insulin-Like Growth Factor Receptor; Proc. Natl. Acad. Sci. USA (1993) vol. 90 pp. 11217-11221.

Shukla, Abhinav, A., et al; Downstream Processing of Monoclonal Antibodies- Application of Platform Approaches; Journal of Chromatography (2007) vol. 848 pp. 28-39.

Srinivasan, Mythily, et al; Immunomodulatory Peptides From IgSF Proteins: A Review; Current Protein and Peptide Science (2005) vol. 6, No. 2 pp. 185-196.

Strumberg, Dirk; Preclinical and Clinical Development of the Oral Multikinase Inhibitor Sorafenib in Cancer Treatment; Drugs of Today (2005) vol. 41, No. 12 pp. 773-784.

Takanami, Iwao, et al; Insulin-Like Growth Factor-II as a Prognostic Factor in Pulmonary Adenocarcinoma; Journal of Surgical Oncology (1996) vol. 61 pp. 205-208.

Tsai, J. F., et al; Serum Insulin-Like Growth Factor-II as a Serologic Marker of Small Hepatollular Carcinoma: Scandinavian Journal of Gastroenterology (2005) vol. 40 pp. 68-75.

Wang, Zheng, et al; Expression of IGF-II in Early Experimental Hepatocellular Carcinomas and its Significance in Early Diagnosis; World Journal of Gastroenterology (2003) vol. 9 pp. 267-270.

(56) References Cited

OTHER PUBLICATIONS

Weroha, S. John et al. "IGF-1 Receptor Inhibitors in Clinical Trials—Early Lessons" J Mammary Gland Biol Neoplasia (2009) vol. 13, (4), 471-483.
Woodson, Karen, et al; Loss of Insulin-Like Growth Factor-II Imprinting and the Presence of Screen-Detected Colorectal Adenomas in Women; Journal of the National Cancer Institute (2004) vol. 96, No. 5 pp. 407-410.
Wu, Henry, et al "Humanization of a Murine Monoclonal Antibody by Simultaneous Optimization of Framework and CDR Residues" (1999) Journal of Molecular Biology vol. 294, pp. 151-162.
Yao, Xiaoming, et al; A Methylated Oligonucleotide Inhibits IGF2 Expression and Enhances Survival in a Model of Hepatocellular Carcinoma; The Journal of Clinical Investigation (2003) vol. 111, No. 2 pp. 265-273.
Yao, Xiaoming, et al; A Novel Orthotopic Tumor Model to Study Growth Factors and Oncogenes in Hepatocarcinogenesis; Clinical Cancer Research (2003) vol. 9 pp. 2719-2726.
Yelton, Dale, E. et al; Affinity Maturation of the BR96 Anti-Carcinoma Antibody by Codon-Based Mutagenesis; The American Association of Immunologists (1995) vol. 155 pp. 1994-2004.
Zapata, Gerardo, et al; Engineering Linear F(ab')2 Fragments for Efficient Production in *Escherichia coli* and Enhanced Antiproliferative Activity; Protein Engineering (1995) vol. 8, No. 10 pp. 1057-1062.
Zhao, Ronghua, et al; Positive Correlation of Insulin-Like Growth Factor-II with Proliferating Cell Index in Patients with Colorectal Neoplasia; Cancer Epidemiology, Biomarkers and Prevention (2005) vol. 14 pp. 1819-1822.
Rota, Lauren M. et al. "Crosstalk of the insulin-like growth factor receptor with the Wnt signaling pathway in breast cancer" Frontiers in Endocrinology, Jun. 2015, vol. 6, Article 92, 5 pgs.
Beattie, James et al. "Cross-Talk Between the Insulin-Like Growth Factor (IGF) Axis and Membrane Integrins to Regulate Cell Physiology" Journal of Cellular Physiology (2010), pp. 605-611.
Barbas, Carlos F., et al; In Vitro evolution of a Neutralizing Human Antibody to Human Immunodeficiency Virus Type 1 to Enhance Affinity and Broaden Strain Cross-Reactivity; Proc. Natl. Acad. Sci. USA (1994) vol. 91 pp. 3809-1813.
Burtrum, Douglas, et al; A Fully Human Monoclonal Antibody to the Insulin-Like Growth Factor I Receptor Blocks Ligand-dependent Signaling and Inhibits Human Tumor Growth in Vivo; Cancer Research (2003) vol. 63 pp. 8912-8921.
Cascieri, Margaret, A., et al; Identification of the Insulin-Like Growth Factor I (IGF I) Epitopes Recognized by Monoclonal and Polyclonal Antibodies to IGF I; Endocrinology (1990) vol. 126, No. 6 pp. 2773-2777.
Casset, Florence et al. "A peptide mimetic of an anti-CD4 monoclonal antibody by rational design" Biochemical and Biophysical Research Communications, (2003) vol. 307, pp. 198-205.
Chen, Jian-Wen, et al; Free Rather than Total Circulating Insulin-Like Growth Factor-I Determines the Feedback on Growth Hormone Release on Normal Subjects; The Journal of Clinical Endocrinology & Metabolism (2005) vol. 90, No. 1 pp. 366-371.
Chen, Yvonne, et al. "Selection and Analysis of an Optimized Anti-VEGF Antibody: Crystal Structure of an Affinity-matured Fab in Complex with Antigen" Journal of Molecular Biology, (1999) vol. 293, pp. 865-881.
Chothia, Cyrus, et al; Canonical Structures for the Hypervariable Regions of Immunoglobulins; Journal Molecular Biology (1987) vol. 196 pp. 901-917.
Cui, Hengmi, et al; Loss of IGF2 Imprinting: A Potential Marker of Colorectal Cancer Risk; Science (2003) vol. 299 pp. 1753-1755.
De Pascails, Roberto, et al. "Grafting of "Abbreviated" Complementarity-Determining Regions Containing Specificity-Determining Residues Essential for Ligand Contact to Engineer a Less Immunogenic Humanized Monoclonal Antibody" The Journal of Immunology (2002) vol. 169 pp. 3076-3084.

Dufner, Almut, et al; Ribosomal S6 Kinase Signaling and the Control of Translation; Experimental Cell Research (1999) vol. 253 pp. 100-109.
European Search Report for EP 07110587.8. Date of completion: Mar. 18, 2008. pp. 1-9.
Feng, Yang, et al; Novel Human Monoclonal Antibodies to Insulin-Like Growth Factor (IGF)-II That Potently Inhibit be IGF Receptor Type I Signal Transduction Function; Molecular Cancer Therapy (2006) vol. 5, No. 1 pp. 114-120.
Frasca, F., et al; Insulin Receptor Isoform A, a Newly Recognized, High-Affinity Insulin-Like Growth Factor II Receptor in Fetal and Cancer Cells; Molecular and Cellular Biology (1999) vol. 19, No. 5 pp. 3278-3288.
Freier, S., et al; Expression of the Insulin-Like Growth Factors and their Receptors in Adenocarcinoma of the Colon; Gut (1999) vol. 44 pp. 704-708.
Fukuzawa, Ryuji, et al; High Frequency of Inactivation of the Imprinted H19 gene in "Sporadic" Hepatoblastoma; International Journal of Cancer (1999) vol. 82 pp. 490-497.
Goetsch, Liliane, et al; A Recombinant Humanized Anti-Insulin-Like Growth Factor Receptor Type I Antibody (h7C10) Enhances the Antitumor Activity of Vinorelbine and Anti-Epidermal Growth Factor Receptor Therapy Against Human Cancer Xenografts; International Journal of Cancer (2005) vol. 113 pp. 316-328.
Goya, Masato, et al; Growth Inhibition of Human Prostate Cancer Cells in Human Adult Bone implanted into Nonobese Diabetic/Severe Combined Immunodeficient Mice by a Ligand-Specific Antibody to Human Insulin-Like Growth Factors; Cancer Research, American Association for Cancer Research (2004) vol. 64, No. 17 pp. 6252-6258.
Green, Larry L. "Antibody engineering via genetic engineering of the mouse: XenoMouse strains are a vehicle for be facile generation of therapeutic human monoclonal antibodies" Journal of Immunological Methods, (1999) vol. 231, pp. 11-23.
Haenel, Cornelia et al; Characterization of High-Affinity Anitbodies by Electrochemiluminescense-Based Equilibrium Titration; (Analytical Biochemistry (2005) vol. 339 pp. 182-184.
Hassan, A. Bassim., et al; Insulin-Like Growth factor II Supply Modifies growth of Intestinal Adenoma in ApcMin/+ Mice1; Cancer Research (2000) vol. 60 pp. 1070-1076.
Hawkins, Robert E., et al; Selection of Phage Antibodies by Binding Affinity Mimicking Affinity Maturation; Journal Mol. Biol. (1992) vol. 226 pp. 889-896.
International Search Report and Written Opinion for corresponding application PCT/EP2015/051308, dated May 27, 2015.
Jackson, Jeffrey R., et al; In Vitro Antibody Maturation: Improvement of a High Affinity, Neutraizing Antibody Against IL-1b; Journal of Immunology (1995) vol. 154, No. 7 pp. 3310-3319.
Jerome L, et al; Deregulation of the IGF Axis in Cancer: Epidemiological Evidence and Potential Therapeutic Interventions; Endocrine-Related Cancer (2003) vol. 10 pp. 561-578.
Jirtle Randy L. "IGF2 Loss of Imprinting: A Potential Heritable Risk Factor for Colorectal Cancer"; Gastroenterology (2004) vol. 126 pp. 1190-1201.
Kipriyanov, Sergey M., et al; Generation and Production of Engineered Antibodies; Molecular Biotechnology (2004) vol. 26 pp. 39-60.
Knappik, Achim, et al; Fully Synthetic Human Combinatorial Antibody Libraries (HuCAL) Based on Modular Consensus Frameworks and CDRs Randomized with Trinucleotides; Journal Molecular Biology (2000) vol. 296 pp. 57-86.
Kolb, E. Anders, et al; Initial Testing (Stage 1) of a Monoclonal Antibody (SCH 717454) Against the IGF-1 Receptor by the Pediatric Preclinical Testing Program; Pediatr Blood Cancer (2008) vol. 50 pp. 1190-1197.
Krebs, Barbara, et al. "High-throughput generation and engineering of recombinant human antibodies" Journal of Immunological Methods 254 (2001) pp. 67-84.
Kulik, George et al; Antiapoptotic Signalling by the Insulin-Like Growth Factor I receptor, Phosphatidylinositol 3-Kinase, and AKt; Molecular and Cellular Biology (1997) vol. 17, No. 3 pp. 1595-1606.
Leroith, Derek; The Insulin-Like Growth Factor System; Experimental Diab. Res. (2003) vol. 4 pp. 205-212.
Li, Shu-Rui, et al; Differential Expression Patterns of the Insulin-Like Growth Factor 2 Gene in Human Colorectal Dancer; Tumor Biology (2004) vol. 25 pp. 62-68.

(56) References Cited

OTHER PUBLICATIONS

Lin, Yvonne, S., et al; Preclinical Pharmacokinetics, Interspecies scaling, and Tissue Distribution of a Humanized Monoclonal Antibody Against Vascular endothelial growth Factor; The Journal of Pharmacology and Experimental Thepapeutics (1999) vol. 288 pp. 371-378.
Lowman, Henry, B., et al; Selecting High-Affiniy Binding Proteins by Monovalent Phage Display; Biochemistry (1991) vol. 30, No. 45 pp. 10832-10837.
Lund, Per, et al; Autocrine Inhibition of Chemotherapy Response in Human Liver Tumor Cells by Insulin-Like Growth Factor-II; Cancer Letters (2004) vol. 206 pp. 85-96.
MacCallum, Robert M. et al. "Antibody-antigen Interactions: Contact Analysis and Binding Site Topography" Journal of Molecular Biology (1996) vol. 262, pp. 732-745.
Manara, Maria C., et al; Preclinical in Vivo Study of New Insulin-Like Growth Factor-I Receptor-Specific Inhibitor in Ewing's Sarcoma; Clinical Cancer Research (2007) vol. 13, No. 4 pp. 1322-1330.
Manes, Santos, et al; Functional Epitope Mapping of Insulin-Like Growth Factor I (IGF-I) by Anti-IGF-I Monoclonal Antibodies; Endocrinology (1997) vol. 138, No. 3 pp. 905-915.
Manes, Santos, et al; Physical Mapping of Human Insulin-Like Growth Factor-I Using Specific Monoclonal Antibodies; Journal of endocrinology (1997) vol. 154 pp. 293-302.
Marks, James D., et al; By-Passing Immunization: Building High Affinity Human Antibodies by Chain Shuffling; Bio/Technology (1992) vol. 10 779-783.
MD Anderson News Release; "Combination of Everolimus and Exemestane Improves Progression-Free Survival for Women with Metastatic Breast Cancer" Dec. 7, 2011; 2 pgs.
Miyamoto, Shin'ichi, et al; Blockade of Paracrine Supply of Insulin-Like Growth Factors Using Neutralizing Antibodies Suppresses the Liver Metastasis of Human Colorectal Cancers; Clin Cancer Research (2005) vol. 11, No. 9 pp. 3494-3502.
Moorehead, Roger A., et al; Transgenic Overexpression of IGF-II Induces Spontaneous Lung Tumors: A Model or Human Lung Adenocarcinoma: Oncogene (2003) vol. 22 pp. 853-857.
Morrell, D.J. et al. "A monoclonal antibody to human insulin-like growth factor -I: characterization, use in adioimmunoassay and effect on the biological activities of the growth factor" Journal of Endocrinology (1989) 2, pp. 201-206.
Nagy, Zoltan A., et al; Fully Human, HLA -DR-Specific Monoclonal Anitbodies efficiently Induce Programmed Death of Malignant Lymphoid Cells; Nature Medicine (2002) vol. 8, Issue 8 pp. 801-807.
Ng, Irene OL, et al; "Hepatocellular Carcinoma Expression of Insulin-Like Growth Factor II mRNA in Hepatocellula Carcinoma" Journal of Gastroenterology and Hepatology (1998) vol. 13, p. 152-157.
European Search Report for corresponding application EP13158228.0, dated Aug. 9, 2013.
Fahrenholtz et al., Targeting 3 IGF-IR with Ganitumab Inhibits Tumorigenesis and Increases Durability of Response to Androgen-Deprivation Therapy in VCaP Prostate Cancer Xenografts, Molecular Cancer Therapeutics, vol. 12, No. 4, 2013, pp. 394-404.
Gao, Jin et al. "Dual IGF-I/II—Neutralizing Antibody Medi-573 Potently Inhibits IGF Signaling and Tumor Growth" (2011) Cancer Research, vol. 71(3), 1029-1040.
Hussain et al., A phase II randomized study of cixutumumab (IMC-AI2: CIX) or ramucirumab (IMC-11218: RAM) plus mitoxantrone (M) and prednisone (P) in patients (pts) with metastatic castrate-resistant prostate cancer (mCRPC) following disease progression (PD) on docetaxel (OCT) therapy, Journal of Clinical Oncology, 2012. Retrieved from the Internet: [retrieved on Jul. 24, 2013] URL:http://meeting.ascopubs.org/cgi/content/abstract/30/5_suppl/97?sid=e7985e77-14e7-47d5-adb0-50acf8bcee69.
Ireland, Lucy et al. "Chemoresistance in Pancreatic Cancer is Driven by Stroma-Derived Insulin-Like Growth Tactors" Cancer Research, (2016) vol. 76, No. 23, 6851-6863.
Martinez-Quetglas, Iris et al "IGF2 is Up-regulated by Epigenetic Mechanisms in Hepatocellular Carcinomas and is an Actionable Oncogene Product in Experimental Models" (2016) Gastroenterology, vol. 151, 1192-1205.
N.N. et al., Bicalutamide and Goserelin or Leuprolide Acetate with or without Cixutumumab in treating patients with newly diagnosed metastatic prostate cancer, ClinicalTrials.gov, 2013 Retrieved from the Internet: URL:http://clinicaltrials.gov/show/NCT01120236 [retrieved on Jul. 24, 2013].
Ohmori, Tohru et al. "Combination effect of afatinib and BI836845, a humanized IGF ligand-neutralizing antibody, on EGFR-TKI-resistant NSCLC cells" 1208, (2016) AACR poster, 1 pg.
Ozkan et al., Plasma and tissue insulin-like growth factor-I receptor (IGF—IR) as a prognostic marker for prostate cancer and anti-IGF-IR agents as novel therapeutic strategy for refractory cases: A review, Molecular and Cellular Endocrinology, vol. 344, No. 1, 2011, pp. 1-24.
Pandini et al., Androgens Up-regulate the Insulin-like Growth Factor-I Receptor in Prostate Cancer Cells, Cancer Research, vol. 65, No. 5, 2005, pp. 1849-1857.
Park, Ji Hyun et al ."Activation of the IGF1R Pathway Potentially Mediates Acquired Resistance to Mutant-Selective 3rd-generation EGF Receptor Tyrosine Kinase Inhibitors in Advanced Non-Small Cell Lung Cancer" Oncotarget (2016) vol. 7, No. 16, 22005-22015.
Weyer-Czernilofsky, Ulrike et al. "Xentuzumab, a humanized IGF-1 and IGF-2 ligand co-neutralizing monoclonal antibody, improves the anti-tumor efficacy of enzalutamide in preclinical models of prostrate cancer" (2017) #20, poster, AACR Annual Meeting, 1 pg.
Who Drug Information, "Recommended INN: List 76, Xentuzumab", (2016) vol. 30, No. 3, pp. 541-542.
Yamaoka, Toshimitsu et al. "Acquired Resistance Mechanisms to Combination Met-TKI/EGFR-TKI Exposure in Met-Amplified EGFR-TKI-Resistant Lung Adenocarcinoma Harboring an Activating EGFR Mutation" (2016) Molecular Cancer Therapy, vol. 15, No. 12, 3040-3054.
Arcaro, Alexandre "Targeting the insulin-like growth factor-1 receptor in human cancer" (2013) Frontiers in Pharmacology, vol. 4, Article 30, 1-8.
Buttigliero, Consuelo et al. "Understanding and overcoming the mechanisms of primary and acquired resistance to abiraterone and enzalutamide in castration resistant prostate cancer" (2015) Cancer Treatment Reviews, 41, 884-892.
Henricks, Linda M. et al. "The use of combinations of monoclonal antibodies in clinical oncology" (2015) Cancer Treatment Reviews, 41, 859-867.
Korenchuk, Susan et al. "VCaP, A Cell-Based Model System of Human Prostate Cancer" (2001) In Vivo, 15, 163-168.
Pritchard, Kathleen I et al. "Safety and Efficacy of Everolimus with Exemestane vs. Exemestane Alone in Elderly Patients with HER2-Negative, Hormone Receptor- Positive Breast Cancer in BOLERO-2" (2013) Clinical Breast Cancer, 421-432.e8.
Puchner, M.J.A. et al. "Tamoxifen Sensitivity-Testing of Glioblastomas: Comparison of in Vitro and in Vivo Results" (2001) Acta Neurochirurgica, 143: 563-573.
Robertson, John F.R. et al. "Ganitumab with either exemestane or fulvestrant for postmenopausal women with advanced, hormone-receptor-positive breast cancer: a randomised, controlled, double-blind, phase 2 trial" (2013) Lancet Oncol. 14, 228-235.
Rocca, Andrea et al. "Palbociclib (PD 0332991): targeting the cell cycle machinery in breast cancer" (2014) Expert Opinion on Pharmacotherapy, 15:3, 407-420.
Ryan, PD et al. "P1-17-01: Figitumumab Plus Exemestane Verus Exemestane as First-Line Treatment of Postmenopausal Hormone Receptor-Positive Advanced Breast Cancer: A Randomized, Open-Label Phase II Trial" Poster Session Abstracts (2011) 3 pgs.
Schweizer, Michael T. et al. "Abiraterone and other novel androgen-directed strategies for the treatment of prostate cancer: a new era of hormonal therapies is born" (2012) Therapeutic Advances in Urology, 4(4) 167-178.
Vander Ark, Alexandra et al. "Mechanisms and Approaches for Overcoming Enzalutamide Resistance in Prostate Cancer" (2018) Frontiers in Oncology, vol. 8, Article 180, 8 pgs.

* cited by examiner

SEQUENCE LISTING

```
<160> NUMBER OF SEQ ID NOS: 46

<210> SEQ ID NO 1
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 1

Asn Tyr Trp Met His
1               5

<210> SEQ ID NO 2
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 2

Gly Ile Ser Gly Trp Ser Ser Trp Thr Tyr Tyr Ala Asp Ser Val Lys
1               5                   10                  15

Gly

<210> SEQ ID NO 3
```

```
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 3

Phe Gly Ile Asp Ala Tyr Thr Lys Val Tyr Phe Asp Tyr
1               5                   10

<210> SEQ ID NO 4
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 4

Ser Gly Asp Asn Ile Pro Leu Lys Tyr Val Ser
1               5                   10

<210> SEQ ID NO 5
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 5

Asp Asp Asn Lys Arg Pro Ser
1               5

<210> SEQ ID NO 6
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 6

Gln Ser Trp Ala Ser Thr Gly Val Val
1               5

<210> SEQ ID NO 7
<211> LENGTH: 122
<212> TYPE: PRT
<213> ORGANISM: Homo sapiens
<220> FEATURE:
<221> NAME/KEY: SOURCE
<222> LOCATION: 1..122
<223> OTHER INFORMATION: /mol_type="protein"
      /organism="Homo sapiens"

<400> SEQUENCE: 7

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
```

```
            20                  25                  30
Trp Met His Trp Val Arg Gln Ala Pro Gly Lys Gly Leu Glu Trp Val
         35                  40                  45
Ser Gly Ile Ser Gly Trp Ser Ser Trp Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
             85                  90                  95
Ala Arg Phe Gly Ile Asp Ala Tyr Thr Lys Val Tyr Phe Asp Tyr Trp
             100                 105                 110
Gly Gln Gly Thr Leu Val Thr Val Ser Ser
         115                 120

<210> SEQ ID NO 8
<211> LENGTH: 107
<212> TYPE: PRT
<213> ORGANISM: Homo sapiens
<220> FEATURE:
<221> NAME/KEY: SOURCE
<222> LOCATION: 1..107
<223> OTHER INFORMATION: /mol_type="protein"
      /organism="Homo sapiens"

<400> SEQUENCE: 8

Asp Ile Glu Leu Thr Gln Pro Pro Ser Val Ser Val Ala Pro Gly Gln
 1               5                  10                  15
Thr Ala Arg Ile Ser Cys Ser Gly Asp Asn Ile Pro Leu Lys Tyr Val
             20                  25                  30
Ser Trp Tyr Gln Gln Lys Pro Gly Gln Ala Pro Val Leu Val Ile His
         35                  40                  45
Asp Asp Asn Lys Arg Pro Ser Gly Ile Pro Glu Arg Phe Ser Gly Ser
 50                  55                  60
Asn Ser Gly Asn Thr Ala Thr Leu Thr Ile Ser Gly Thr Gln Ala Glu
 65                  70                  75                  80
Asp Glu Ala Asp Tyr Tyr Cys Gln Ser Trp Ala Ser Thr Gly Val Val
             85                  90                  95
Phe Gly Gly Gly Thr Lys Leu Thr Val Leu Gly
             100                 105

<210> SEQ ID NO 9
<211> LENGTH: 452
<212> TYPE: PRT
<213> ORGANISM: Homo sapiens
<220> FEATURE:
<221> NAME/KEY: SOURCE
<222> LOCATION: 1..452
<223> OTHER INFORMATION: /mol_type="protein"
      /organism="Homo sapiens"

<400> SEQUENCE: 9

Gln Val Glu Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Asn Tyr
             20                  25                  30
Trp Met His Trp Val Arg Gln Ala Pro Gly Lys Gly Leu Glu Trp Val
         35                  40                  45
Ser Gly Ile Ser Gly Trp Ser Ser Trp Thr Tyr Tyr Ala Asp Ser Val
 50                  55                  60
```

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 10
<211> LENGTH: 212
<212> TYPE: PRT

-continued

```
<213> ORGANISM: Homo sapiens
<220> FEATURE:
<221> NAME/KEY: SOURCE
<222> LOCATION: 1..212
<223> OTHER INFORMATION: /mol_type="protein"
      /organism="Homo sapiens"

<400> SEQUENCE: 10
```

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Ala Ser Thr Gly Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Gly Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Thr Glu Cys Ser
    210

```
<210> SEQ ID NO 11
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 11
```

Asn Tyr Trp Met His
1               5

```
<210> SEQ ID NO 12
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 12
```

```
Gly Ile Ser Gly Trp Ser Ser Trp Thr Tyr Tyr Ala Asp Ser Val Lys
1               5                   10                  15

Gly

<210> SEQ ID NO 13
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 13

Phe Gly Ile Asp Ala Tyr Thr Lys Val Tyr Phe Asp Tyr
1               5                   10

<210> SEQ ID NO 14
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 14

Ser Gly Asp Asn Ile Pro Leu Lys Tyr Val Ser
1               5                   10

<210> SEQ ID NO 15
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 15

Asp Asp Asn Lys Arg Pro Ser
1               5

<210> SEQ ID NO 16
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 16

Ser Ser Trp Asp Thr Leu Asp Ile Phe Asn Val
1               5                   10

<210> SEQ ID NO 17
<211> LENGTH: 122
<212> TYPE: PRT
<213> ORGANISM: Homo sapiens
<220> FEATURE:
<221> NAME/KEY: SOURCE
<222> LOCATION: 1..122
<223> OTHER INFORMATION: /mol_type="protein"
```

/organism="Homo sapiens"

<400> SEQUENCE: 17

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ser Gly Ile Ser Gly Trp Ser Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser
        115                 120

<210> SEQ ID NO 18
<211> LENGTH: 109
<212> TYPE: PRT
<213> ORGANISM: Homo sapiens
<220> FEATURE:
<221> NAME/KEY: SOURCE
<222> LOCATION: 1..109
<223> OTHER INFORMATION: /mol_type="protein"
      /organism="Homo sapiens"

<400> SEQUENCE: 18

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Asp Thr Leu Asp Ile Phe
                85                  90                  95

Asn Val Phe Gly Gly Gly Thr Lys Leu Thr Val Leu Gly
            100                 105

<210> SEQ ID NO 19
<211> LENGTH: 452
<212> TYPE: PRT
<213> ORGANISM: Homo sapiens
<220> FEATURE:
<221> NAME/KEY: SOURCE
<222> LOCATION: 1..452
<223> OTHER INFORMATION: /mol_type="protein"
      /organism="Homo sapiens"

<400> SEQUENCE: 19

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr

-continued

```
            20                  25                  30
Trp Met His Trp Val Arg Gln Ala Pro Gly Lys Gly Leu Glu Trp Val
                35                  40                  45
Ser Gly Ile Ser Gly Trp Ser Ser Trp Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Phe Gly Ile Asp Ala Tyr Thr Lys Val Tyr Phe Asp Tyr Trp
            100                 105                 110
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Lys Val Glu Pro Lys Ser
        210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
        290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
            355                 360                 365
Ser Leu Thr Cys Leu Val Lys Gly Phe Tyr Pro Ser Asp Ile Ala Val
        370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
```

Ser Pro Gly Lys
    450

<210> SEQ ID NO 20
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 20

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Asp Thr Leu Asp Ile Phe
                85                  90                  95

Asn Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 21
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 21

Asn Tyr Trp Met His
1               5

<210> SEQ ID NO 22
<211> LENGTH: 17
<212> TYPE: PRT

```
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 22

Gly Ile Ser Gly Trp Ser Ser Trp Thr Tyr Tyr Ala Asp Ser Val Lys
1               5                   10                  15
Gly

<210> SEQ ID NO 23
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 23

Phe Gly Ile Asp Ala Tyr Thr Lys Val Tyr Phe Asp Tyr
1               5                   10

<210> SEQ ID NO 24
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 24

Ser Gly Asp Asn Ile Pro Leu Lys Tyr Val Ser
1               5                   10

<210> SEQ ID NO 25
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 25

Asp Asp Asn Lys Arg Pro Ser
1               5

<210> SEQ ID NO 26
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
      /organism="Homo sapiens"

<400> SEQUENCE: 26

Gln Ser Tyr Asp Tyr Phe Pro Lys Phe Val Val
1               5                   10
```

-continued

```
<210> SEQ ID NO 27
<211> LENGTH: 122
<212> TYPE: PRT
<213> ORGANISM: Homo sapiens
<220> FEATURE:
<221> NAME/KEY: SOURCE
<222> LOCATION: 1..122
<223> OTHER INFORMATION: /mol_type="protein"
      /organism="Homo sapiens"

<400> SEQUENCE: 27
```

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ser Gly Ile Ser Gly Trp Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser
        115                 120

```
<210> SEQ ID NO 28
<211> LENGTH: 109
<212> TYPE: PRT
<213> ORGANISM: Homo sapiens
<220> FEATURE:
<221> NAME/KEY: SOURCE
<222> LOCATION: 1..109
<223> OTHER INFORMATION: /mol_type="protein"
      /organism="Homo sapiens"

<400> SEQUENCE: 28
```

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Tyr Phe Pro Lys Phe
                85                  90                  95

Val Val Phe Gly Gly Gly Thr Lys Leu Thr Val Leu Gly
            100                 105

```
<210> SEQ ID NO 29
<211> LENGTH: 452
<212> TYPE: PRT
<213> ORGANISM: Homo sapiens
<220> FEATURE:
<221> NAME/KEY: SOURCE
<222> LOCATION: 1..452
<223> OTHER INFORMATION: /mol_type="protein"
```

/organism="Homo sapiens"

<400> SEQUENCE: 29

```
Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ser Gly Ile Ser Gly Trp Ser Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Ile Asp Ala Tyr Thr Lys Val Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450
```

<210> SEQ ID NO 30
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 30

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Pro Leu Lys Tyr Val
            20                  25                  30

Ser Trp Tyr Gln Gln Lys Pro Gly Gln Ala Pro Val Leu Val Ile His
        35                  40                  45

Asp Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Tyr Phe Pro Lys Phe
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 31
<211> LENGTH: 5
<212> TYPE: PRT
<213> ORGANISM: Homo sapiens
<220> FEATURE:
<221> NAME/KEY: SOURCE
<222> LOCATION: 1..5
<223> OTHER INFORMATION: /mol_type="protein"
      /organism="Homo sapiens"

<400> SEQUENCE: 31

```
Ser Tyr Trp Met Ser
1               5

<210> SEQ ID NO 32
<211> LENGTH: 17
<212> TYPE: PRT
<213> ORGANISM: Homo sapiens
<220> FEATURE:
<221> NAME/KEY: SOURCE
<222> LOCATION: 1..17
<223> OTHER INFORMATION: /mol_type="protein"
      /organism="Homo sapiens"

<400> SEQUENCE: 32

Ser Ile Thr Ser Tyr Gly Ser Phe Thr Tyr Tyr Ala Asp Ser Val Lys
1               5                   10                  15

Gly

<210> SEQ ID NO 33
<211> LENGTH: 8
<212> TYPE: PRT
<213> ORGANISM: Homo sapiens
<220> FEATURE:
<221> NAME/KEY: SOURCE
<222> LOCATION: 1..8
<223> OTHER INFORMATION: /mol_type="protein"
      /organism="Homo sapiens"

<400> SEQUENCE: 33

Asn Met Tyr Thr His Phe Asp Ser
1               5

<210> SEQ ID NO 34
<211> LENGTH: 13
<212> TYPE: PRT
<213> ORGANISM: Homo sapiens
<220> FEATURE:
<221> NAME/KEY: SOURCE
<222> LOCATION: 1..13
<223> OTHER INFORMATION: /mol_type="protein"
      /organism="Homo sapiens"

<400> SEQUENCE: 34

Ser Gly Ser Ser Ser Asn Ile Gly Ser Asn Ser Val Ser
1               5                   10

<210> SEQ ID NO 35
<211> LENGTH: 7
<212> TYPE: PRT
<213> ORGANISM: Homo sapiens
<220> FEATURE:
<221> NAME/KEY: SOURCE
<222> LOCATION: 1..7
<223> OTHER INFORMATION: /mol_type="protein"
      /organism="Homo sapiens"

<400> SEQUENCE: 35

Asp Asn Ser Lys Arg Pro Ser
1               5

<210> SEQ ID NO 36
<211> LENGTH: 11
<212> TYPE: PRT
<213> ORGANISM: Homo sapiens
<220> FEATURE:
<221> NAME/KEY: SOURCE
<222> LOCATION: 1..11
<223> OTHER INFORMATION: /mol_type="protein"
```

/organism="Homo sapiens"

<400> SEQUENCE: 36

Gln Ser Arg Asp Thr Tyr Gly Tyr Tyr Trp Val
1               5                   10

<210> SEQ ID NO 37
<211> LENGTH: 117
<212> TYPE: PRT
<213> ORGANISM: Homo sapiens
<220> FEATURE:
<221> NAME/KEY: SOURCE
<222> LOCATION: 1..117
<223> OTHER INFORMATION: /mol_type="protein"
      /organism="Homo sapiens"

<400> SEQUENCE: 37

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Trp Met Ser Trp Val Arg Gln Ala Pro Gly Lys Gly Leu Glu Leu Val
        35                  40                  45

Ser Ser Ile Thr Ser Tyr Gly Ser Phe Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Met Tyr Thr His Phe Asp Ser Trp Gly Gln Gly Thr Leu
            100                 105                 110

Val Thr Val Ser Ser
        115

<210> SEQ ID NO 38
<211> LENGTH: 111
<212> TYPE: PRT
<213> ORGANISM: Homo sapiens
<220> FEATURE:
<221> NAME/KEY: SOURCE
<222> LOCATION: 1..111
<223> OTHER INFORMATION: /mol_type="protein"
      /organism="Homo sapiens"

<400> SEQUENCE: 38

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Asp Asn Ser Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Arg Asp Thr Tyr Gly
                85                  90                  95

Tyr Tyr Trp Val Phe Gly Gly Gly Thr Lys Leu Thr Val Leu Gly
            100                 105                 110

-continued

```
<210> SEQ ID NO 39
<211> LENGTH: 447
<212> TYPE: PRT
<213> ORGANISM: Homo sapiens
<220> FEATURE:
<221> NAME/KEY: SOURCE
<222> LOCATION: 1..447
<223> OTHER INFORMATION: /mol_type="protein"
      /organism="Homo sapiens"

<400> SEQUENCE: 39

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Trp Met Ser Trp Val Arg Gln Ala Pro Gly Lys Gly Leu Glu Leu Val
        35                  40                  45

Ser Ser Ile Thr Ser Tyr Gly Ser Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Met Tyr Thr His Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
```

```
                355                 360                 365
Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 40
<211> LENGTH: 216
<212> TYPE: PRT
<213> ORGANISM: Homo sapiens
<220> FEATURE:
<221> NAME/KEY: SOURCE
<222> LOCATION: 1..216
<223> OTHER INFORMATION: /mol_type="protein"
      /organism="Homo sapiens"

<400> SEQUENCE: 40

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Asp Asn Ser Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Arg Asp Thr Tyr Gly
                85                  90                  95

Tyr Tyr Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Gly Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 41
<211> LENGTH: 121
<212> TYPE: PRT
<213> ORGANISM: Homo sapiens
<220> FEATURE:
<221> NAME/KEY: SOURCE
```

<222> LOCATION: 1..121
<223> OTHER INFORMATION: /mol_type="protein"
      /organism="Homo sapiens"

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Tyr Tyr Tyr Tyr Gly Met Asp Val Trp Gly Gln
            100                 105                 110

Gly Thr Thr Val Thr Val Ser Ser Ala
        115                 120

<210> SEQ ID NO 42
<211> LENGTH: 112
<212> TYPE: PRT
<213> ORGANISM: Homo sapiens
<220> FEATURE:
<221> NAME/KEY: SOURCE
<222> LOCATION: 1..112
<223> OTHER INFORMATION: /mol_type="protein"
      /organism="Homo sapiens"

<400> SEQUENCE: 42

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Glu Asn Asn
            20                  25                  30

His Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Thr Ser Leu
                85                  90                  95

Ser Ala Gly Arg Val Phe Gly Gly Thr Lys Leu Thr Val Leu Gly
            100                 105                 110

<210> SEQ ID NO 43
<211> LENGTH: 121
<212> TYPE: PRT
<213> ORGANISM: Homo sapiens
<220> FEATURE:
<221> NAME/KEY: SOURCE
<222> LOCATION: 1..121
<223> OTHER INFORMATION: /mol_type="protein"
      /organism="Homo sapiens"

<400> SEQUENCE: 43

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Tyr Tyr Tyr Tyr Gly Met Asp Val Trp Gly Gln Gly
            100                 105                 110

Gly Thr Thr Val Thr Val Ser Ser Ala
        115                 120
```

<210> SEQ ID NO 44
<211> LENGTH: 112
<212> TYPE: PRT
<213> ORGANISM: Homo sapiens
<220> FEATURE:
<221> NAME/KEY: SOURCE
<222> LOCATION: 1..112
<223> OTHER INFORMATION: /mol_type="protein"
      /organism="Homo sapiens"

<400> SEQUENCE: 44

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Glu Asn Asn
            20                  25                  30

His Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Thr Ser Leu
                85                  90                  95

Ser Ala Gly Arg Val Phe Gly Gly Gly Thr Lys Leu Thr Val Leu Gly
            100                 105                 110
```

<210> SEQ ID NO 45
<211> LENGTH: 450
<212> TYPE: PRT
<213> ORGANISM: Homo sapiens
<220> FEATURE:
<221> NAME/KEY: SOURCE
<222> LOCATION: 1..450
<223> OTHER INFORMATION: /mol_type="protein"
      /organism="Homo sapiens"

<400> SEQUENCE: 45

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Thr Thr Phe Tyr Ala Asp Ser Val
```

```
            50                  55                  60
Lys Gly Arg Phe Thr Ile Ser Arg Asp Asn Ser Arg Thr Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Gly Trp Ser Asp Ser Tyr Tyr Tyr Tyr Gly Met
                100                 105                 110

Asp Val Trp Gly Gln Gly Thr Thr Val Thr Val Ser Ser Ala Ser Thr
                115                 120                 125

Lys Gly Pro Ser Val Phe Pro Leu Ala Pro Cys Ser Arg Ser Thr Ser
                130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Asn Phe Gly Thr Gln Thr Tyr Thr Cys
                195                 200                 205

Asn Val Asp His Lys Pro Ser Asn Thr Lys Val Asp Lys Thr Val Glu
210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Gln Phe Asn Trp Tyr Val Asp Gly Val Glu Val
                275                 280                 285

His Asn Ala Lys Thr Lys Pro Arg Glu Glu Gln Phe Asn Ser Thr Phe
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
450

<210> SEQ ID NO 46
```

```
<211> LENGTH: 214
<212> TYPE: PRT
<213> ORGANISM: Homo sapiens
<220> FEATURE:
<221> NAME/KEY: SOURCE
<222> LOCATION: 1..214
<223> OTHER INFORMATION: /mol_type="protein"
      /organism="Homo sapiens"

<400> SEQUENCE: 46

Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

COMBINATION THERAPY FOR NEOPLASIA TREATMENT

The present invention relates to the pharmaceutical treatment of neoplasia, including benign and malignant tumors.

BACKGROUND OF THE INVENTION

Prostate cancer is the most common malignancy diagnosed in males and a leading cause of mortality in western countries (American Cancer Society, 2010 (http://www.cancer.org/acs/groups/content/@epidemiologysurveilance/documents/document/acspc-026238.pdf)). Androgens and stimulation of their receptor, androgen receptor (AR), are essential for the development and function of the normal prostate gland, and the development and progression of prostate cancer (reviewed in Basu S et al., Horm Cancer. 2010 October; 1(5):223-8.; Yadav N et al., Minerva Urol Nefrol. 2012 March; 64(1):35-49). For metastatic prostate cancer, androgen deprivation therapy remains the standard treatment. Despite the fact that initially more than 90% of patients respond to androgen deprivation therapy, the clinical benefits are temporary with tumors becoming refractory and progressing to androgen-independent/castration-resistant prostate cancer (CRPC) (Rini B I et al., Curr Treat Options Oncol. 2002 October; 3(5):437-46.; Carles J et al., Clin Transl Oncol. 2012 March; 14(3):169-76). CRPC is associated with continued androgen receptor (AR) activation despite hormonal castration and/or treatment with currently available anti-androgens. The molecular mechanism of androgen stimulation of prostate cancer growth and the switch to androgen independence is not fully clear. The progression to androgen independence may be explained by changes with the androgen receptor, such as amplification, mutations, or altered activity of splice variants. Other possible mechanisms include tumor cell autonomous production of androgens, ligand-independent activation of AR by kinases like ERK or AKT (reviewed in Dutt S S et al., Future Oncol. 2009 November; 5(9):1403-13. and Attar R M et al., Clin Cancer Res. 2009 May 15; 15(10):3251-5) or that androgens may regulate prostate cancer proliferation by up-regulating autocrine loops involving peptide growth factors and their cognate receptors (De Bellis A et al., J Clin Endocrinol Metab 1996; 81:4148-54.). All these mechanisms could result in independence to endocrine androgens.

Benign prostatic hyperplasia (BPH) can be detected in the vast majority of men as they age (Parsons J K., Curr Bladder Dysfunct Rep. 2010 December; 5(4):212-218). BPH can be defined as a non-cancerous enlargement of the prostate resulting from a proliferation of both benign stromal, and to a lesser extent, epithelial cells (Foster C S. Prostate 2000; 9:4-14.). In both of these cell types, dihydrotestosterone (DHT), a metabolite of testosterone that is 10 times more potent because it dissociates from the androgen receptor more slowly than testosterone, binds to nuclear androgen receptors resulting in the transcription of growth factors that are mitogenic to the epithelial and stromal cells. In the prostate, testosterone is converted to DHT by the enzyme 5α-reductase, type 2. In the condition of BPH, local testosterone levels can be elevated more than 100-fold above serum levels leading to an increased availability of DHT (Gat Y et al., Andrologia 2008 October; 40(5):273-81). Therapy with 5α-reductase inhibitors, such as finasteride, markedly reduces the DHT content of the prostate and, in turn, reduces prostate volume and, in many cases, BPH symptoms. Androgens are thought to be essential for BPH to occur, but do not seem to be the only cause for the condition.

Insulin-like growth factors(IGFs) and their binding proteins may play an important role in understanding the etiology of prostate disease, including BPH. Several lines of evidence support involvementof the IGF axis in BPH. IGF ligands have mitogenic effects on the prostate, while IGF binding proteins (IGFBPs) are growth inhibitory due to their ability to regulate availability of the IGFs, other growth factors, and steroid hormones (Pollak M N et al, Nat Rev 2004; 4:505-518.). IGFBP3 is secreted at particularly low levels in stromal cells in BPH tissue (Boudon C et al., J Clin Endocrinol Metab 1996; 81:612-617.) which may favor hyperplastic growth and play a role in the development of BPH. Moreover, acromegalic patients, who have very high levels of IGF1 and concomitantly low levels of testosterone and DHT, present with enlarged prostates and high rates of BPH (Colao A et al J Clin Endocrinol Metab 1999; 84:1986-1991; Colao A et al, Eur J Endocrinol 2000; 143:61-69.).

The insulin-like growth factor (IGF) system plays a key role in stimulating proliferation and survival of both normal tissues and cancers (reviewed in LeRoith D, Roberts C T Jr., Cancer Lett 2003; 195:127-37). High circulating IGF-1 concentrations have been associated with increased risk for prostate cancer in several clinical and epidemiologic studies (Price A J et al., Cancer Epidemiol Biomarkers Prev. 2012 September; 21(9):1531-41; Roddam A W et al., Ann Intern Med 2008; 149(7):461-71). In prostate epithelial cells, increased IGF-1 expression was shown to lead to higher rates of proliferation and/or lower rates of apoptosis (Takahara K et al., Prostate. 2011 April; 71(5):525-37). Loss of imprinting of the IGF-2 locus and increased expression of IGF-2 are observed in many cancers including prostate cancer (Jarrard D F et al., Clinical Cancer Research 1995; 1, 1471-1478.; Fu V X et al., Cancer Research 2008; 68, 6797-6802) and may be related to the risk to develop prostate cancer (Belharazem D et al, Endocrine Connections 2012; 1, 87-94). Furthermore, not only expression of IGF-1 and IGF-2 ligands but also their receptor, IGF-1R, has been shown to be elevated in advanced prostate tumors (Cardillo, M R et al., Anticancer Res. 2003 23, 3825-3835; Liao, Y et al., Hum. Pathol. 2005; 36 (11), 1186-1196; Hellawell G O et al., Cancer Res. 2002 May 15; 62(10):2942-50; Turney B W et al., BJU Int. 2011 May; 107(9):1488-99; Krueckl S L et al., Cancer Res. 2004 Dec. 1; 64(23):8620-9; Figueroa, J A et al., Cancer Invest. 2001; 19 (1), 28-34; Ryan, C J et al., Urol. Oncol. 2007; 25, 134-140). In recurrent and androgen-independent cancer, an increase also in AKT phosphorylation was demonstrated (Graff J R et al., J. Biol. Chem 2000; 275: 24500-5; Murillo H et al., Endocrinology 2001; 142: 4795-805.).

Castration-resistant prostate cancer has been shown to be sensitive, but not resistant, to sustained manipulation of the androgen/AR axis. The androgen axis can be manipulated using anti-androgens (nilutamide, enzalutamide), androgen synthesis inhibitors (ketonazole, abiraterone acetate), corticosteroids (dexamethasone, prednisone) or estrogen treatment. Following the emergence of castration-refractory disease, taxane-based chemotherapy has been shown to be therapeutically efficacious and prolong survival. Patients progressing on docetaxel have been shown to benefit from abiraterone acetate, a selective cytochrome P450 17A1 inhibitor which requires co-administration with glucocorticoids to curtail side effects. Enzalutamide (MDV-3100) is a novel AR antagonist that blocks AR signaling more effectively than currently available AR antagonists (Tran et al., Science 2009; 324(5928): 787-790.) and has shown impressive antitumor activity and a similar impact on overall survival as abiraterone.

Antagonists to IGF action and their use in cancer therapy have been described in the art. For disclosure of IGF receptor tyrosine kinase inhibitors, see WO2009/009016 and WO2010/099139. For disclosure of antibodies against IGF receptor, see WO2002/53596, WO2003/093317, WO2003/106621, WO2006/013472, WO2006/069202. For disclosure of antibodies against IGF ligand, see WO2003/093317, WO2005/028515, WO2007/022172, WO2007/070432, WO2008/155387, WO2009/137758, WO2010/066868. IGF-1 receptor antibodies, WO2008/098917, WO2009/137378) and IGF ligand antibodies (WO2007/118214, WO2008/155387, WO2009/137758, WO2010/066868) have been proposed for use, inter alia, in the treatment of prostate cancer.

The state of the art is also discussed in further publications (Pollak M N et al., Cancer Metastasis Rev 1998; 17:383-90; Djavan B et al., World J Urol 2001; 19:225-33; Wolk A et al., J Natl Cancer Inst 1998; 90:911-5; Jiang Y G et al., Int. J. Urol. 2007; 14:1034-9; Lin H K et al., Proc. Natl Acad. Sci. USA 2001; 98: 7200-5; Wen Y et al., Cancer Res. 2000; 60: 6841-5; Plymate S R et al., Prostate 2004; 61:276-90; A A Lubik et al., Endocr Relat Cancer ERC-12-0250 2013, first published on 14 January; Nickerson T et al. Cancer Res. 2001; 61 (16), 6276-6280; Pandini G et al., Cancer Res., 2005 Mar. 1; 65; 1849; Bedolla R et al. Clin Cancer Res. 2007 Jul. 1; 13(13):3860-7; Carver B S et al., Cancer Cell 2011 May 17; 19, 575-586; Mulholland D J et al., Cancer Cell, 2011 Jun. 14; 19, 792-804)

Despite advances made in the early detection and treatment of prostate neoplasia, including benign prostatic hyperplasia (BPH), prostate cancer, and particularly CRPC, there is a significant need for improvements in therapy.

BRIEF DESCRIPTION OF THE FIGURES

FIGS. 1A-F show the inhibitory effect of the IGF mAb_1 (FIGS. 1A+1C+1E) and IGF mAb_2 (FIGS. 1B+1D+1F) antibodies and MDV-3100, alone and in combination, on the 2D proliferation of prostate cancer-derived VCaP cells (FIGS. 1A+1B), MDA PCa 2b cells (FIGS. 1C+1D) and DUCaP cells (FIGS. 1E+1F) in 10% FCS-containing growth medium. In all three cell lines, single agent treatment with both IGF antibodies and MDV-3100 resulted in inhibition of cell proliferation which could be enhanced by the combination of both agents leading to a complete inhibition of proliferation.

FIG. 2A displays the results of the treatment of VCaP cells with IGF mAb_1 in 2D cell proliferation assays. IGF mAb_2 was used for the treatment of VCaP cells in FIG. 2B. FIG. 2C (IGF mAb_1) and FIG. 2D (IGF mAb_2) show the results of MDA PCa 2b cells. The treatment of DUCaP cells with IGF mAb_1 is displayed in FIG. 2E and with IGF mAb_2 in FIG. 2F. Single agent treatment with IGF mAb_1 and mAb_2 resulted in inhibition of cell proliferation of 70% to 90%. Abiraterone acetate treatment caused inhibition of cell proliferation at higher concentrations which could be enhanced by the combination with either of the antibodies, lowering the doses of AA needed for complete inhibition. In a 3D soft agar cell proliferation assay (FIG. 2G), VCaP cells were treated with abiraterone acetate and IGF mAb_2. Similar to the results observed in 2D, single agent treatment with IGF mAb_2 results in 96% inhibition of cell proliferation. Abiraterone acetate treatment caused inhibition of cell proliferation at higher concentrations which could be enhanced by the combination with IGF mAb_2.

FIGS. 3A-C show the effects of IGF mAb_1 and MDV-3100, alone and in combination, on IGF-1R, AR and PTEN levels, as well as AKT phosphorylation, in VCaP, MDA PCa 2b and DUCaP cells as assessed by Western blot analyses. Cells were seeded in 6-well plates and treated for 24 hours. (FIG. 3A) Lysates prepared from treated VCaP cells were compared to untreated controls and insensitive PC-3 cells for protein expression of IGF-1R, AR, PTEN and AKT and for phosphorylation of AKT-Ser473. Protein expression and AKT phosphorylation of untreated and treated MDA PCa 2b (FIG. 3B) and DUCaP (FIG. 3C) cells were evaluated and compared to that of VCaP cells. Untreated PC-3 cells served as a control. Importantly, VCaP, MDA PCa 2b, and DUCaP cells were shown to express the IGF1-R, AR and PTEN, unlike the insensitive cell line PC-3. MDV-3100 treatment slightly increased AR protein levels which may be due to stabilization of the protein. Concomitantly, IGF-1R levels were slightly decreased upon MDV-3100 treatment. The combination of both agents resulted in a more complete inhibition of AKT phosphorylation than the antibody or MDV-3100 treatment alone.

FIG. 4 demonstrates the effects of IGF mAb_1 and MDV-3100 used as single agents and in combination on IGF-1R levels and AKT phosphorylation in VCaP cells over 120 hours of treatment. VCaP cells were seeded in 6-well plates and treated with MDV-3100 and IGF mAb_1 as single agents or in combination for 24, 48, 72, 96, and 120 hours. Lysates prepared from treated cells were compared to untreated controls for phosphorylation of AKT-Ser473. Combination of both agents resulted in a longer lasting inhibition of AKT phosphorylation than the antibody or MDV-3100 treatments alone.

Proliferation of VCAP cells was monitored using a $H^3$-thymidine incorporation assay. Treated with 10 μM of MDV-3100 or 1 μM of IGF mAb_1 as single agents for 96 hours reduced proliferative activity by approximately 50%. Combination of IGF mAb_1 and MDV-3100 reduced thymidine incorporation by more than 95% compared to untreated controls.

Figure 6A:
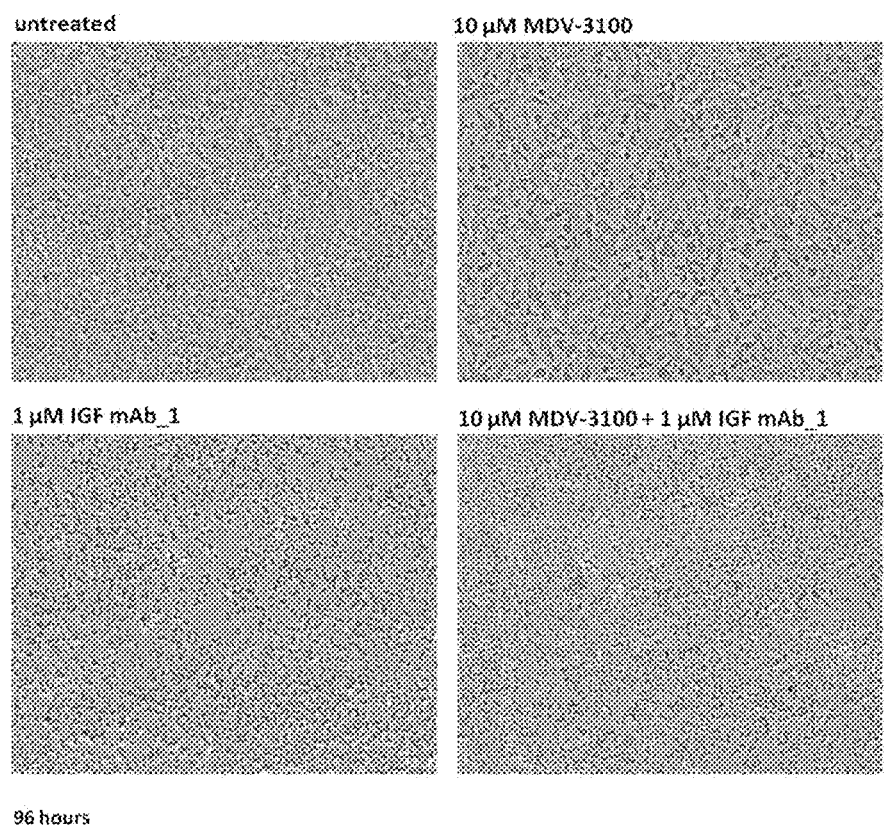
Figure 6B:
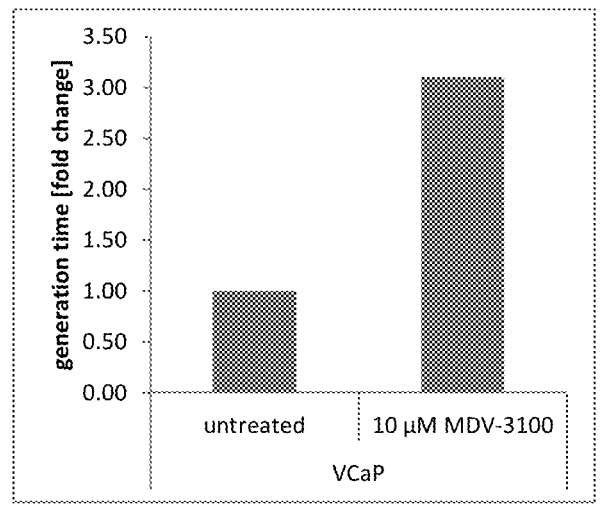

FIG. 6A-B. Diminished growth rate of VCaP cells following single agent and combination treatment of IGF mAb_1 and MDV-3100

FIG. 6A shows the effect of 1 μM of IGF mAb_1 and 10 μM of MDV-3100 used as single agents and in combination on cell morphology and cell growth as observed in microscopic analyses. FIG. 6B shows the effect of 10 μM of MDV-3100 on the generation time of VCaP cells compared to untreated controls.

Figure 7:
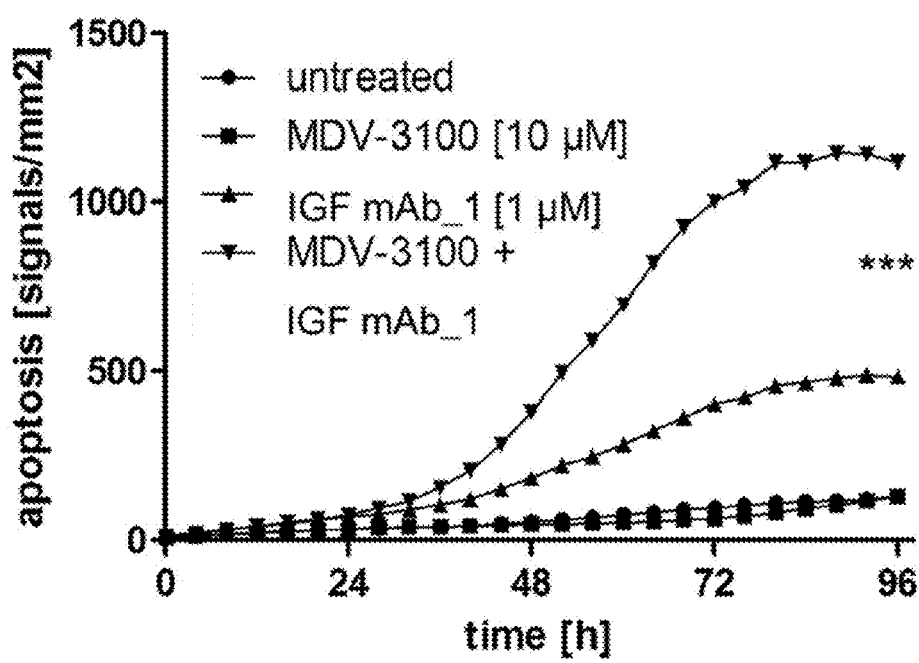

FIG. 7. Combination treatment of IGF mAb_1 and MDV-3100 increases induction of apoptosis in VCaP cells Caspase 3 activity was used as a measure of the induction of apoptosis in VCaP cells upon treatment with 10 μM of MDV-3100 and 1 μM of mAb as single agents and in combination for up to 96 hours. Whereas MDV-3100 treatment did not induce caspase 3 activity within 96 hours of treatment, an increase in apoptotic events were observed upon treatment with IGF mAb_1. The combination of both agents showed a synergistic effect on the induction of caspase 3 activity, which was approximately 9-fold increased compared to controls and approximately 2.5-fold higher compared to IGF mAb_1 treatment.

FIG. 8A-L. Cell cycle profiles of VCaP cells treated with MDV-3100 and IGF mAb_1

Figure 8A:
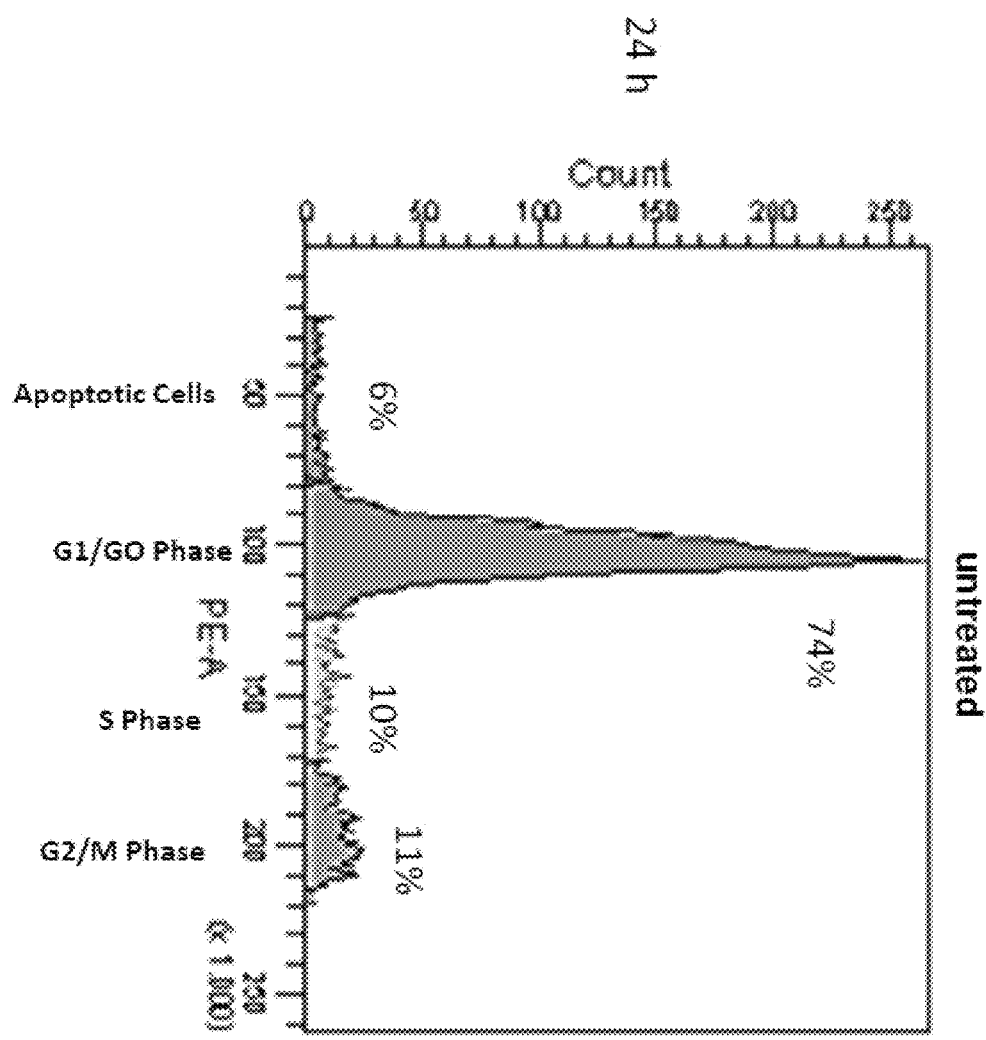
Figure 8B:
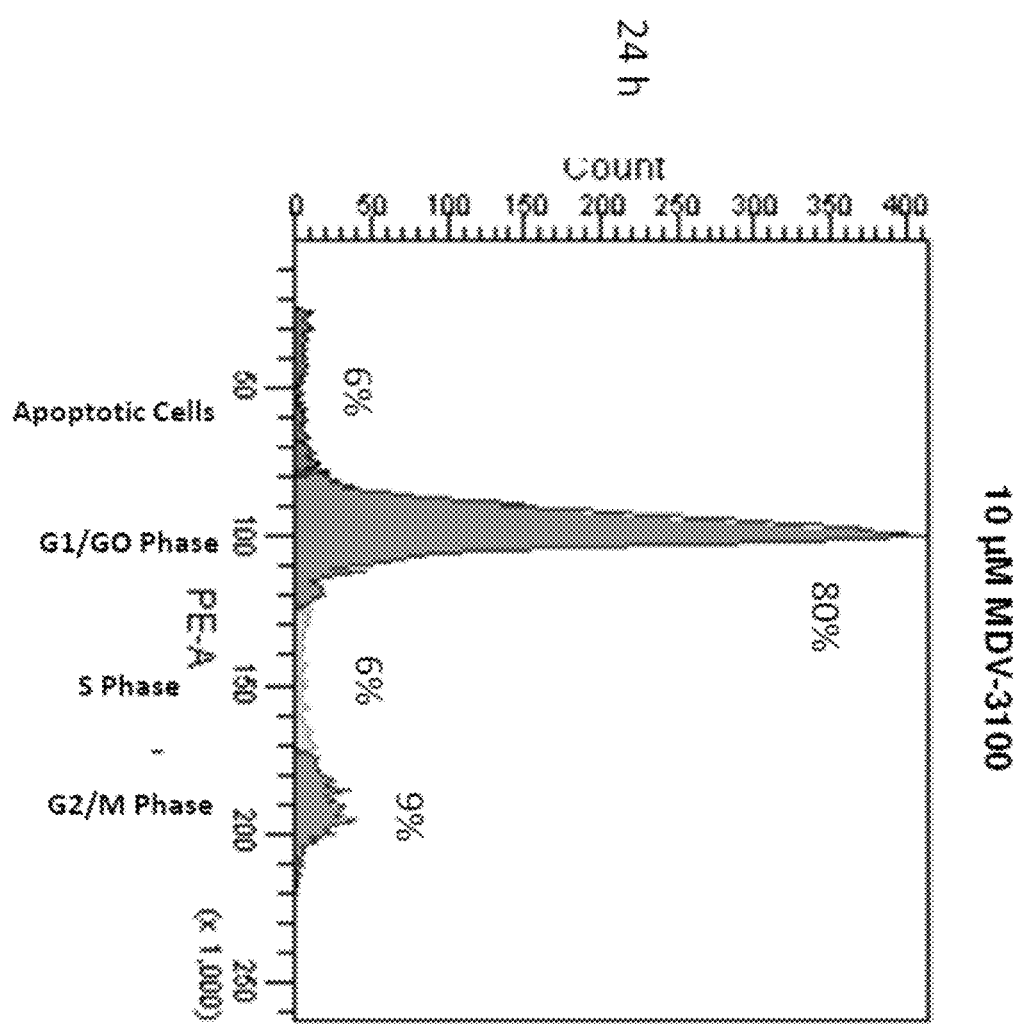
Figure 8C:
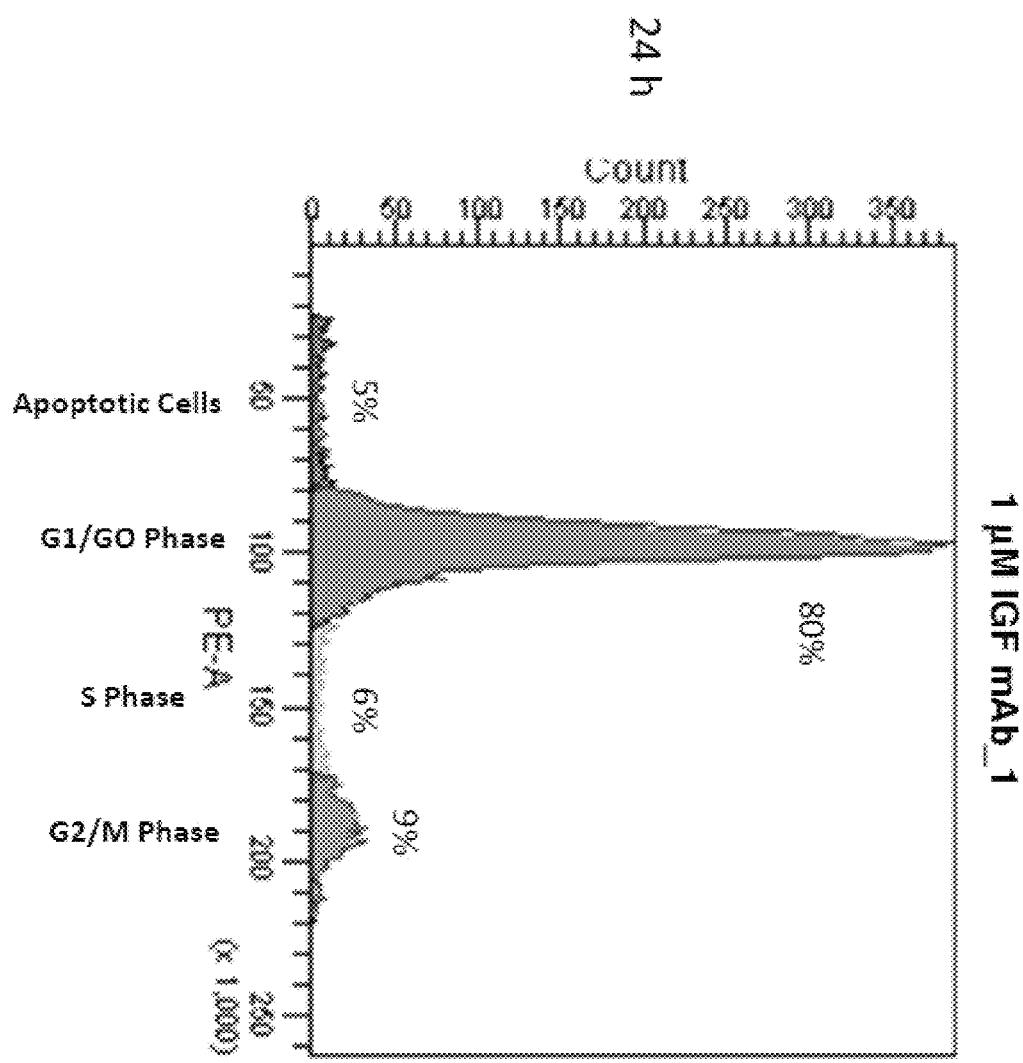
Figure 8D:
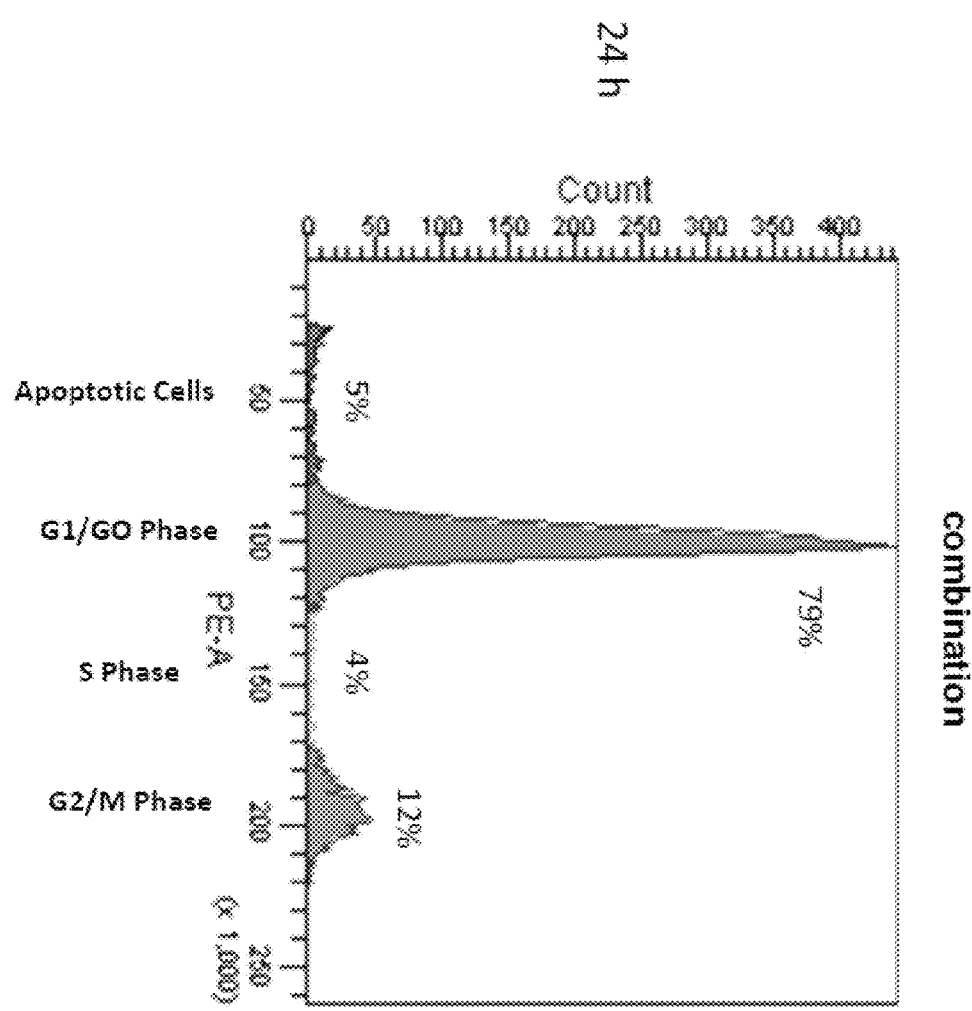
Figure 8E:
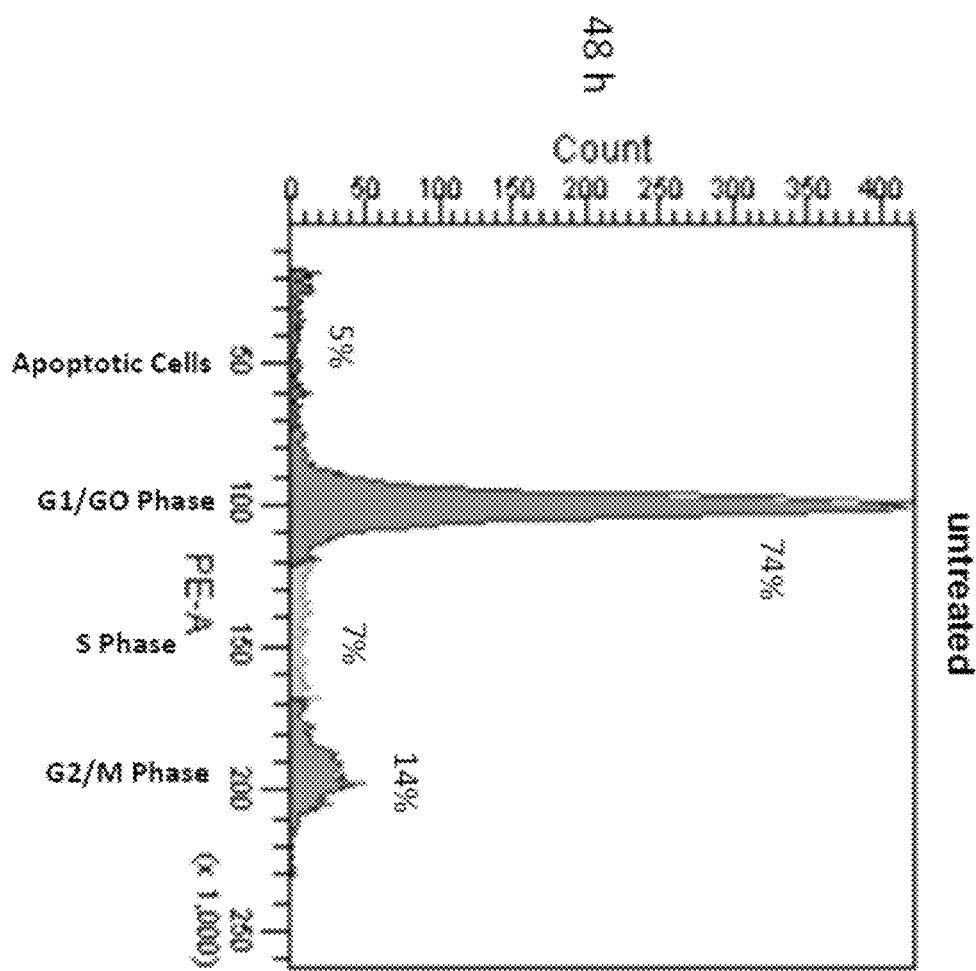
Figure 8F:
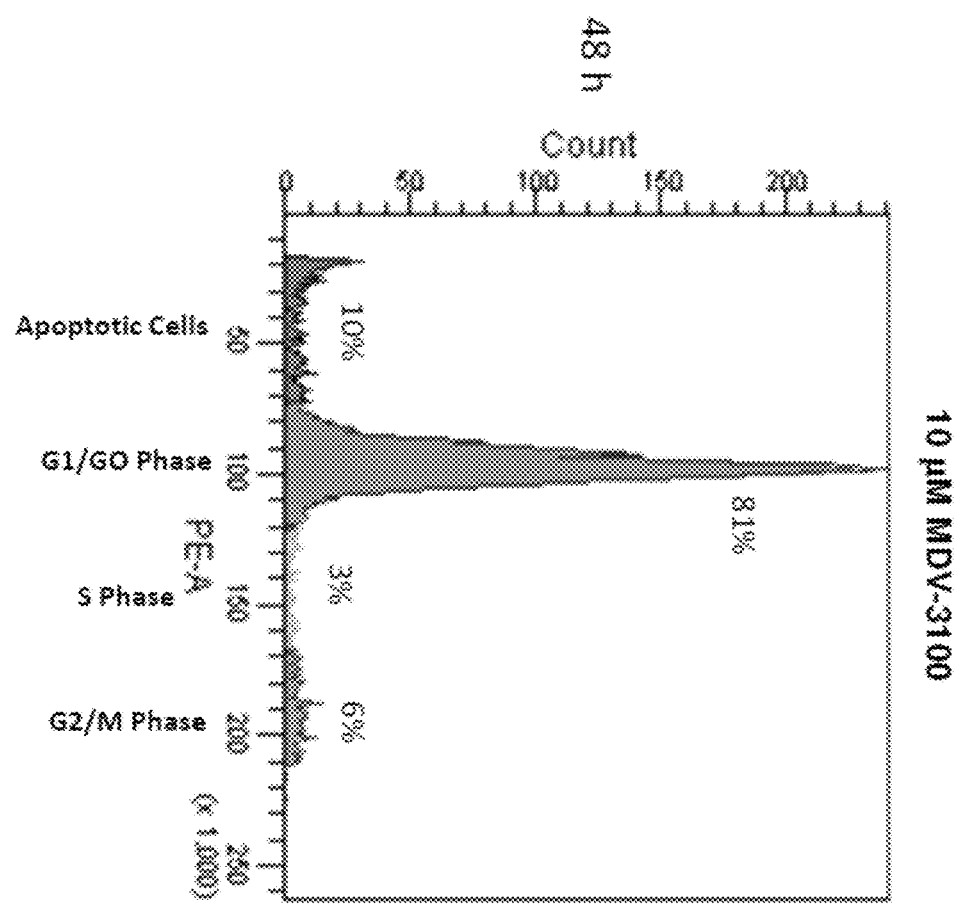
Figure 8G:
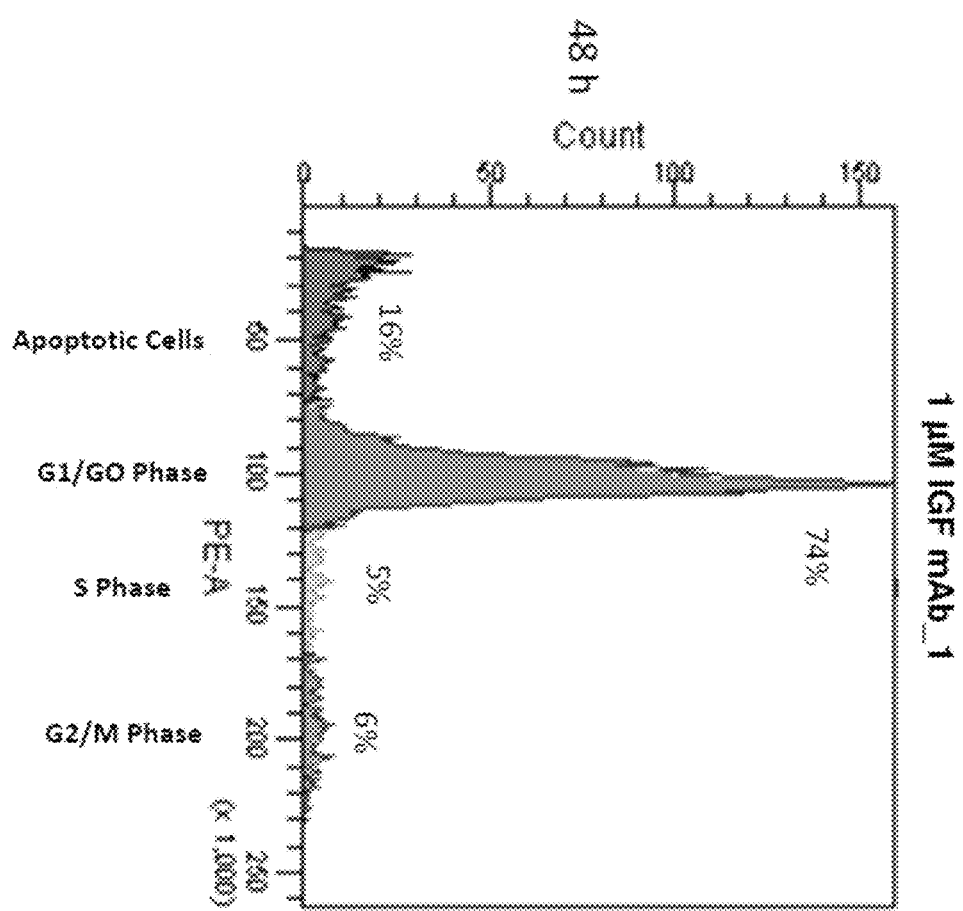
Figure 8H:
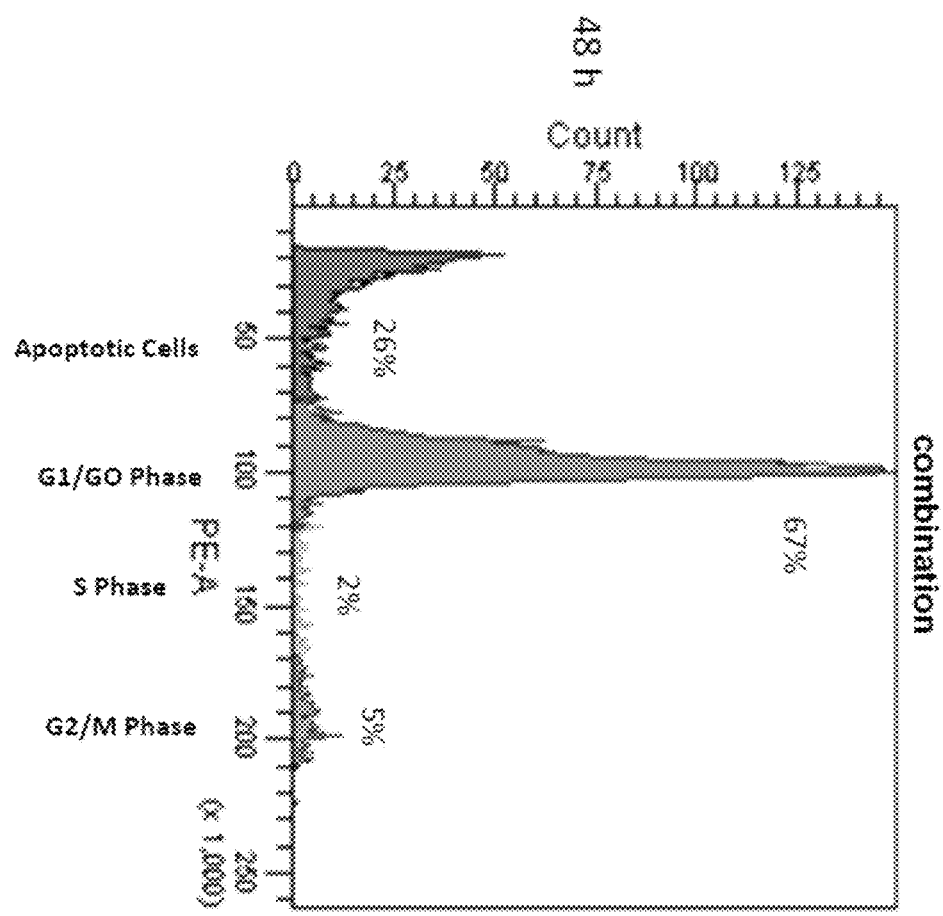
Figure 8I:
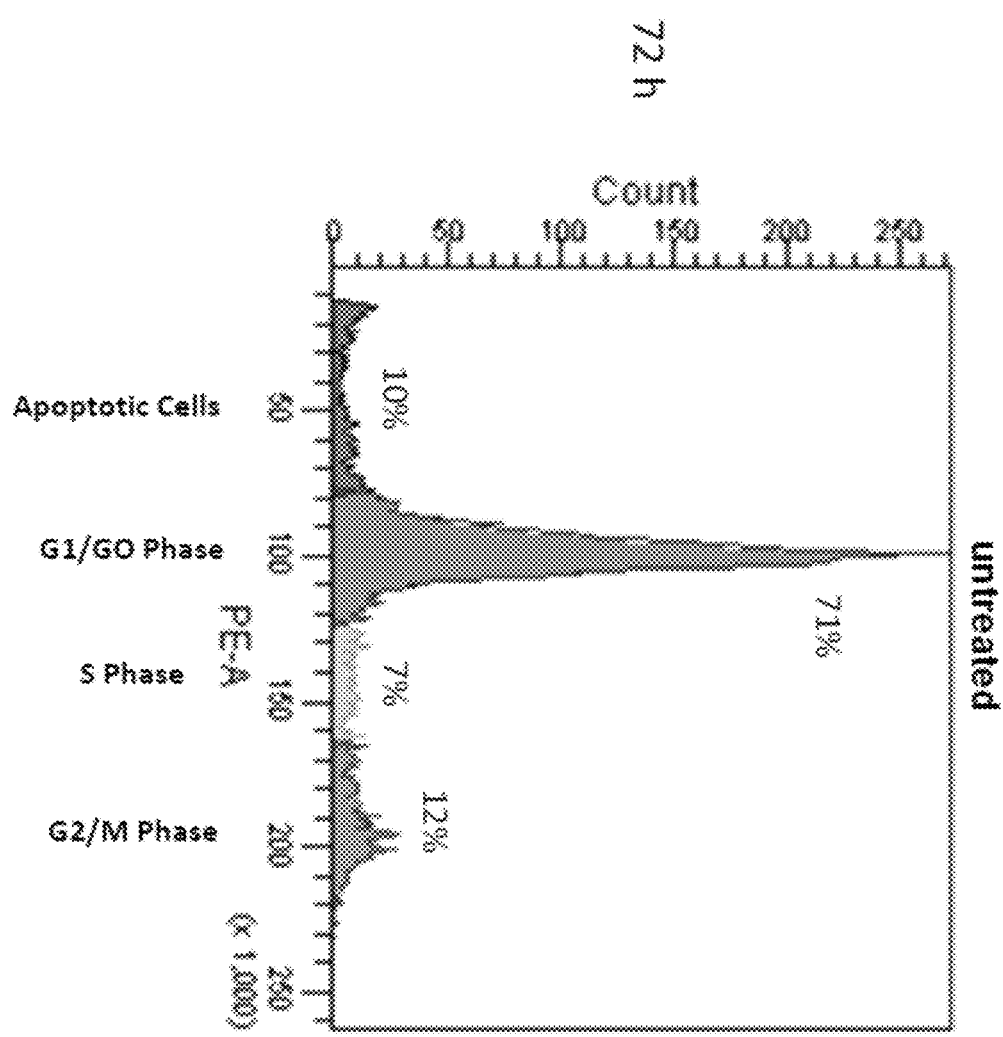
Figure 8J:
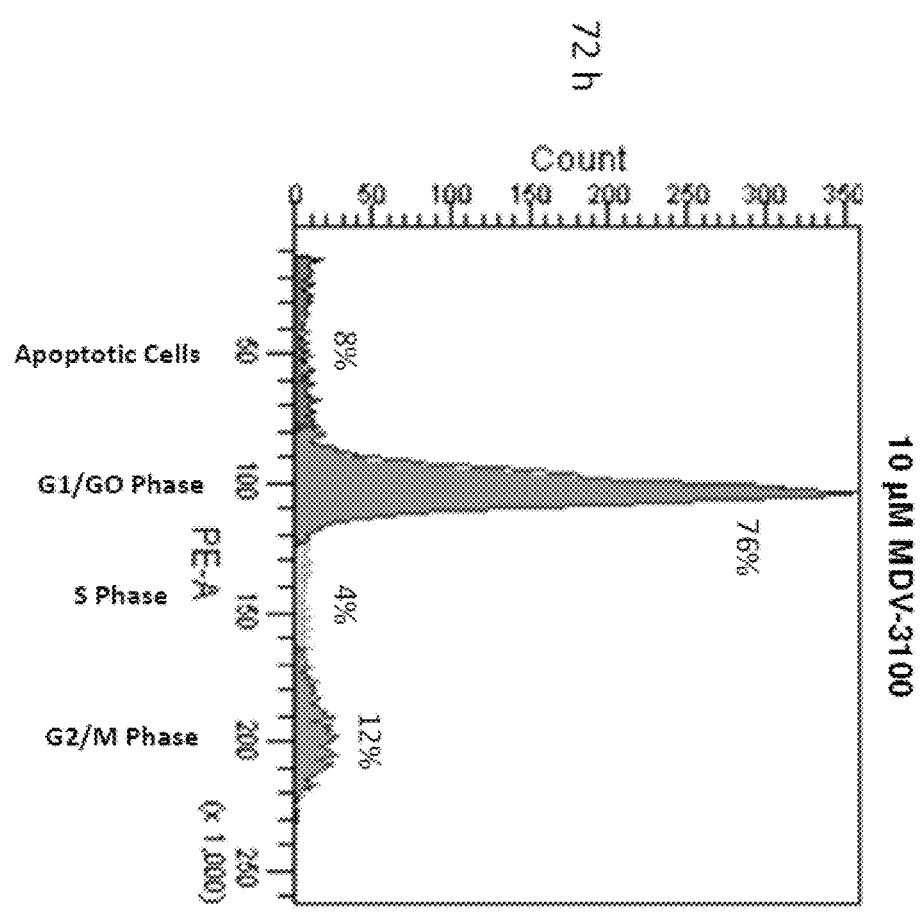
Figure 8K:
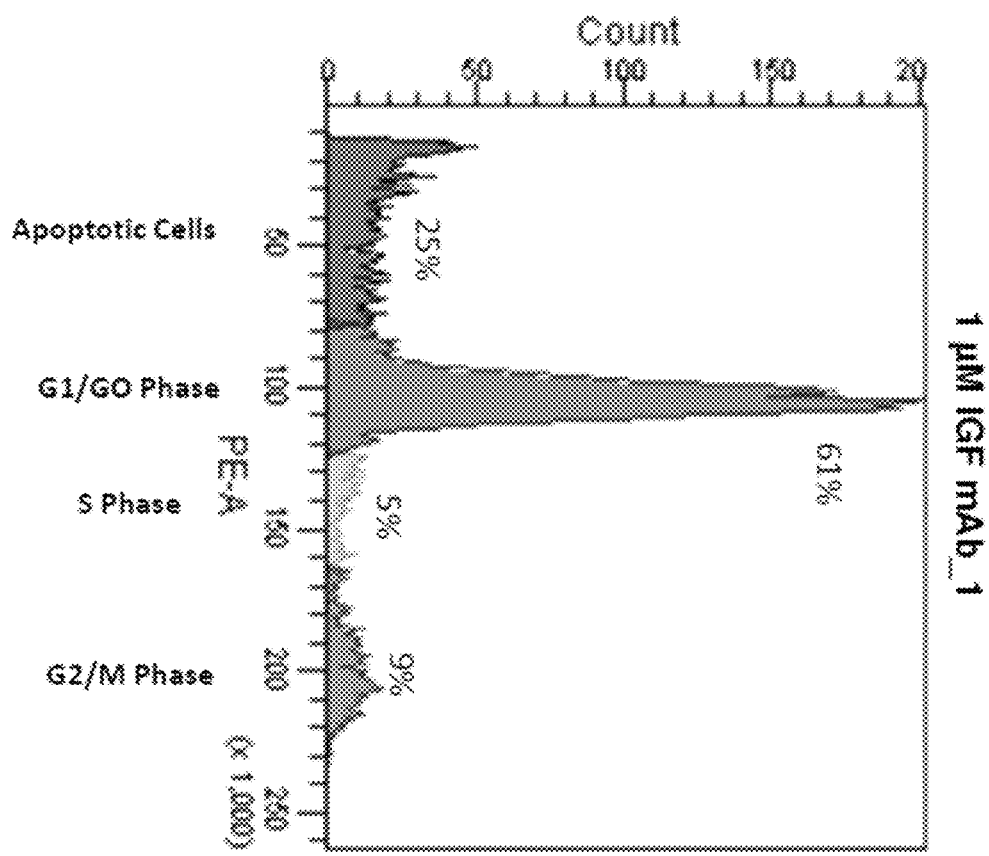
Figure 8L:
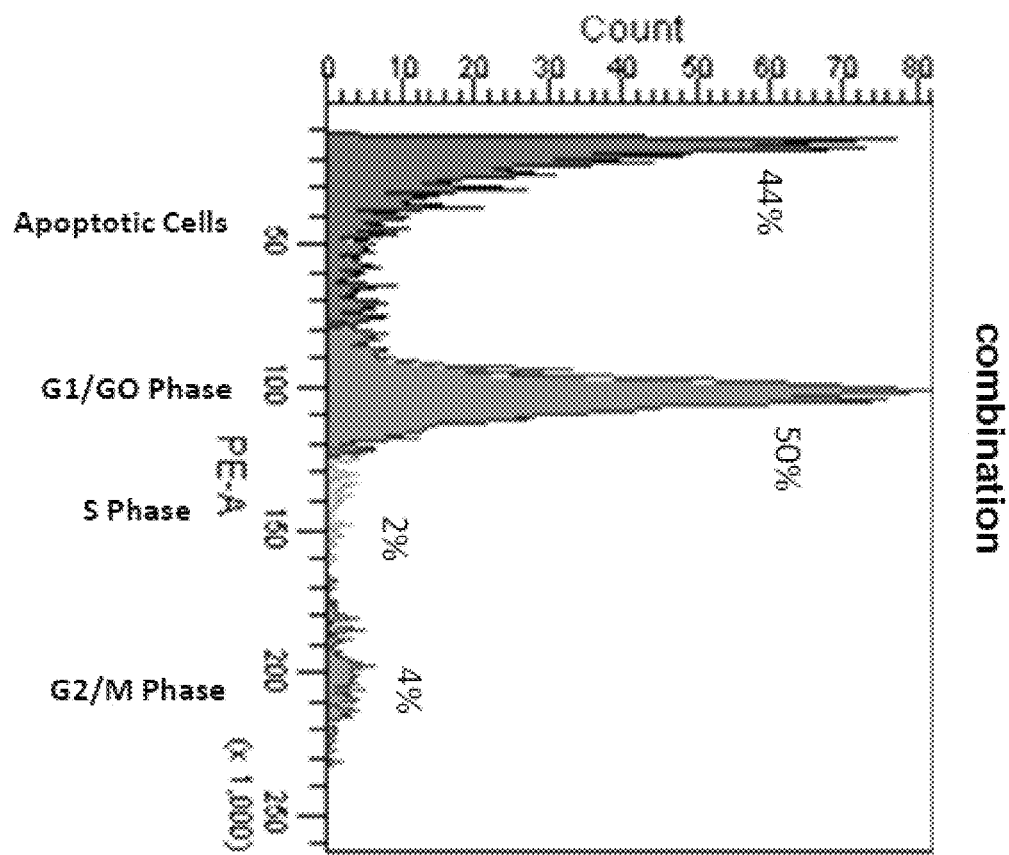

The cell cycle profiles of VCaP cells after 24 h, 48 h and 72 h of treatment with 10 μM of MDV-3100 and 1 μM of mAb as single agents and in combination as determined by propidium iodide staining detected by flow cytometry. FIG. 8A shows cells 24 h untreated. FIG. 8B shows cells 24 h with 10 μM of MDV-3100. FIG. 8C shows cells 24 h with 1 μM of mAb. FIG. 8D shows cells 24 h with combination treatment. FIG. 8E shows cells 48 h untreated. FIG. 8F shows cells 48 h with 10 μM of MDV-3100. FIG. 8G shows cells 48 h with 1 μM of mAb. FIG. 8H shows cells 48 h with combination treatment. FIG. 8I shows cells 72 h untreated. FIG. 8J shows cells 72 h with 10 μM of MDV-3100. FIG. 8K shows cells 72 h with 1 μM of mAb. FIG. 8L shows cells 72 h with combination treatment. The first population to the left is the sub-G1 population representing apoptotic cells, the second population shows the G1/G0 peak, the light grey population shows cells in the S-phase, and the population to the right represents cells in the G2/M-phase of the cell cycle. In VCaP cells treated with IGF mAb_1, and to a greater extent in cells treated with the combination of IGF mAb_1 and MDV-3100 the apoptotic cell population increases with time, whereas in VCaP cells treated with MDV-3100 this population does not change. Instead, MDV-3100 treatment increased the G1/G0 population compared to untreated controls.

Figure 9:
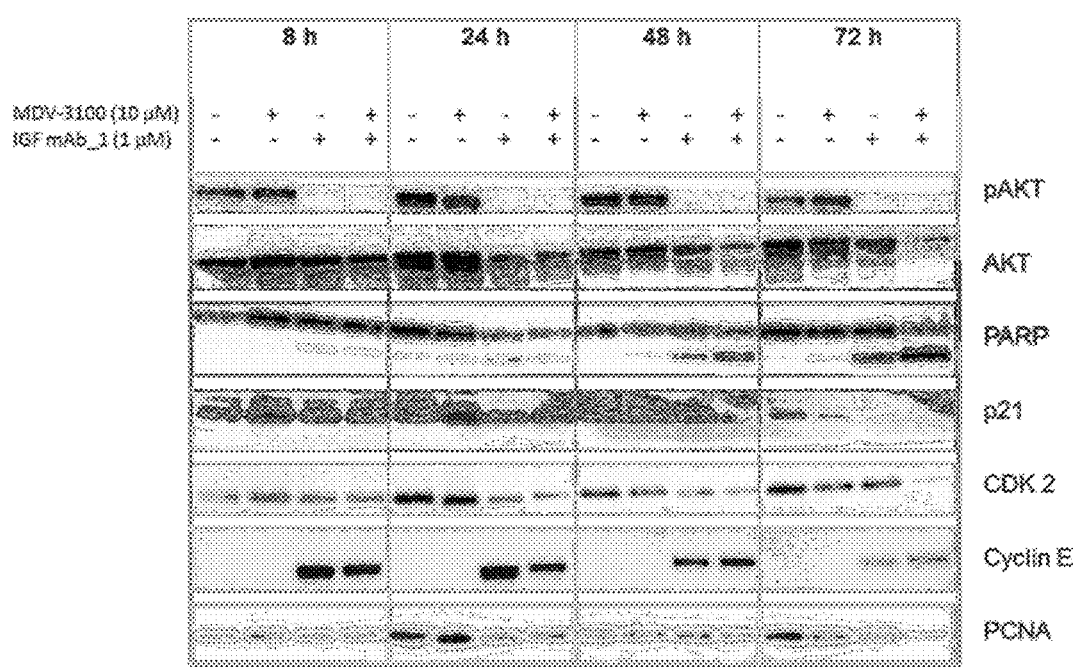

FIG. 9. Protein analysis of apoptosis and cell cycle regulators following IGF signaling inhibition The effects of the treatment with 10 μM of MDV-3100 and 1 μM of IGF mAb_1 as single agents and in combination on AKT phosphorylation, PARP cleavage, p21, CDK2, Cyclin E, and PCNA levels after 8 h, 24 h, 48 h and 72 h of treatment where analyzed by Western blot analysis. IGF mAb_1 treatment led to blockade of AKT phosphorylation, and combined IGF mAb_1 and MDV-3100 treatment increased PARP cleavage and Cyclin E levels while it reduced CDK2 and PCNA levels. MDV-3100 treatment increased p21 levels at 8 and 24 hours.

BRIEF DESCRIPTION OF THE INVENTION

In one aspect, the present invention pertains to an insulin-like growth factor (IGF) receptor antagonist for use in the treatment of prostate neoplasia, including benign prostatic hyperplasia (BPH), prostate cancer, and particularly CRPC in combination with an androgen receptor antagonist.

In another embodiment, the invention relates to a method of treatment of prostate neoplasia, including benign prostatic hyperplasia (BPH), prostate cancer, and particularly CRPC comprising administering a therapeutically effective amount of an IGF receptor antagonist to a patient in need thereof, and additionally administering a therapeutically effective amount of an androgen receptor antagonist to the same patient on the same day, or one, two, three, four, five, six or seven days before or after administration of the IGF receptor antagonist.

DETAILED DESCRIPTION OF THE INVENTION

The present invention relates to the treatment of prostate neoplasia.

By "prostate neoplasia", the aspects of the invention include where the prostate neoplasia is prostate cancer, including benign and malignant tumours, and particularly castration resistant prostate cancer; and also benign prostatic hyperplasia.

In one aspect, the present invention pertains to an insulin-like growth factor (IGF) receptor antagonist for use in the treatment of prostate cancer. In another embodiment, the prostate cancer is hormone-sensitive prostate cancer. In another embodiment, the prostate cancer is prostate cancer after combined androgen blockade. In another embodiment, the prostate cancer is prostate cancer treated with antiangiogenic therapy. In another embodiment the prostate cancer has been, or will be, treated with a chemotherapeutic agent. In another embodiment, the prostate cancer is prostate cancer treated, or will be treated, with radiation therapy. In another embodiment, the prostate cancer is prostate cancer treated, or will be treated, with bone loss therapy, for example denosumab, and hormone ablation.

In another embodiment, the prostate cancer is castration resistant prostate cancer (CRPC). In another embodiment the castration resistant prostate cancer has been, or will be, treated with a chemotherapeutic agent. In another embodiment, the castration resistant prostate cancer has been, or will be, treated with radiation therapy. In another embodiment, the prostate cancer is castration resistant prostate cancer in a pre- or post-docetaxel setting. In another embodiment, the prostate cancer is castration resistant prostate cancer after cabazitaxel treatment. In another embodiment, the prostate cancer is castration resistant prostate cancer after treatment with androgen synthesis inhibitors, for example abiraterone acetate. In another embodiment, the prostate cancer is castration resistant prostate cancer after treatment with androgen receptor antagonists, for example enzalutamide. In another embodiment, the prostate cancer is castration resistant prostate cancer after treatment with immune-modulating agents, for example Sipuleucel-T.

In another aspect, the present invention pertains to an insulin-like growth factor (IGF) receptor antagonist for use in the treatment of prostate cancer incombination with an androgen receptor antagonist. In another embodiment, the prostate cancer is hormone-sensitive prostate cancer. In another embodiment, the prostate cancer is prostate cancer after combined androgen blockade. In another embodiment, the prostate cancer is prostate cancer treated with antiangiogenic therapy. In another embodiment the prostate cancer has been, or will be, treated with a chemotherapeutic agent. In another embodiment, the prostate cancer is prostate cancer treated, or will be treated, with radiation therapy. In another embodiment, the prostate cancer is prostate cancer treated, or will be treated, with bone loss therapy, for example denosumab, and hormone ablation.

In another embodiment, the prostate cancer is castration resistant prostate cancer. In another embodiment the castration resistant prostate cancer has been, or will be, treated with a chemotherapeutic agent. In another embodiment, the castration resistant prostate cancer has been, or will be, treated with radiation therapy. In another embodiment, the prostate cancer is castration resistant prostate cancer in a pre- or post-docetaxel setting. In another embodiment, the prostate cancer is castration resistant prostate cancer after cabazitaxel treatment. In another embodiment, the prostate cancer is castration resistant prostate cancer after treatment with androgen synthesis inhibitors, for example abiraterone acetate. In another embodiment, the prostate cancer is castration resistant prostate cancer after treatment with androgen receptor antagonists, for example enzalutamide. In another embodiment, the prostate cancer is castration resistant prostate cancer after treatment with immune-modulating agents, for example Sipuleucel-T.

In another aspect, the present invention pertains to an insulin-like growth factor (IGF) receptor antagonist for use in the treatment of benign prostatic hyperplasia. In another aspect, the present invention pertains to an insulin-like growth factor (IGF) receptor antagonist for use in the treatment of benign prostatic hyperplasia in combination with an androgen receptor antagonist.

An IGF receptor antagonist within the context of the invention is a compound that interferes with, either directly or indirectly, and reduces or blocks IGF receptor signaling. Preferably, an IGF receptor antagonist is a compound that reduces or blocks binding of IGF ligand to its receptor, or inhibits the tyrosine kinase activity of the IGF receptor.

In a further embodiment, the IGF receptor antagonist of the present invention is an antibody that binds to IGF ligand and thus reduces or prevents binding of the ligand to the receptor. In another embodiment, the IGF receptor antagonist is an antibody that binds to the IGF-1 receptor and thus reduces or prevents binding of the ligand to the receptor. By blocking receptor-ligand binding, ligand-induced receptor signaling through the tyrosine kinase activity of the receptor is reduced or prevented. Such antibodies are generally referred to as neutralizing antibodies. In another aspect, the present invention pertains to an IGF receptor antagonist that neutralizes the growth promoting properties of the insulin-like growth factors, IGF-1 and IGF-2.

The term "antibody" encompasses antibodies, antibody fragments, antibody-like molecules and conjugates with any of the above. Antibodies include, but are not limited to, poly- or monoclonal, chimeric, humanized, human, mono-, bi- or multispecific antibodies. The term "antibody" shall encompass complete immunoglobulins as they are produced by lymphocytes and for example present in blood sera, monoclonal antibodies secreted by hybridoma cell lines, polypeptides produced by recombinant expression in host cells, which have the binding specificity of immunoglobulins or monoclonal antibodies, and molecules which have been derived from such immunoglobulins, monoclonal antibodies, or polypeptides by further processing while retaining their binding specificity. In particular, the term "antibody" includes complete immunoglobulins comprising two heavy chains and two light chains. In another embodiment, the term encompasses a fragment of an immunoglobulin, like Fab fragments. In another embodiment, the term "antibody" encompasses a polypeptide having one or more variable domains derived from an immunobulin, like single chain antibodies (scFv), single domain antibodies, and the like.

In a further embodiment, the IGF receptor antagonist of the invention is an antibody against IGF-1, an antibody against IGF-2, an antibody binding both IGF-1 and IGF-2, an antibody against IGF-1 receptor (IGF-1R), or an inhibitor of IGF-1R tyrosine kinase activity.

In another embodiment, the IGF receptor antagonist is an IGF ligand antibody having heavy chain complementary determining regions of SEQ ID NO: 1 (HCDR1), SEQ ID NO: 2 (HCDR2), and SEQ ID NO: 3 (HCDR3) and light chain determining regions of SEQ ID NO: 4 (LCDR1), SEQ ID NO: 5 (LCDR2), and SEQ ID NO: 6 (LCDR3).

In another embodiment, the IGF receptor antagonist is an IGF ligand antibody having heavy chain complementary determining regions of SEQ ID NO: 11 (HCDR1), SEQ ID NO: 12 (HCDR2), and SEQ ID NO: 13 (HCDR3) and light chain determining regions of SEQ ID NO: 14 (LCDR1), SEQ ID NO: 15 (LCDR2), and SEQ ID NO: 16 (LCDR3).

In another embodiment, the IGF receptor antagonist is an IGF ligand antibody having heavy chain complementary determining regions of SEQ ID NO: 21 (HCDR1), SEQ ID NO: 22 (HCDR2), and SEQ ID NO: 23 (HCDR3) and light chain determining regions of SEQ ID NO: 24 (LCDR1), SEQ ID NO: 25 (LCDR2), and SEQ ID NO: 26 (LCDR3).

In another preferred embodiment, the IGF receptor antagonist is an IGF ligand antibody having heavy chain complementary determining regions of SEQ ID NO: 31 (HCDR1), SEQ ID NO: 32 (HCDR2), and SEQ ID NO: 33 (HCDR3) and light chain determining regions of SEQ ID NO: 34 (LCDR1), SEQ ID NO: 35 (LCDR2), and SEQ ID NO: 36 (LCDR3). An example of an antibody containing these complementary determining regions is designated herein as IGF mAb_1.

In another embodiment, the IGF receptor antagonist is an IGF ligand antibody having a heavy chain variable region of SEQ ID NO: 7 and a light chain variable region of SEQ ID NO: 8.

In another embodiment, the IGF receptor antagonist is an IGF ligand antibody having a heavy chain variable region of SEQ ID NO: 17 and a light chain variable region of SEQ ID NO: 18.

In another embodiment, the IGF receptor antagonist is an IGF ligand antibody having a heavy chain variable region of SEQ ID NO: 27 and a light chain variable region of SEQ ID NO: 28.

In another preferred embodiment, the IGF receptor antagonist is an IGF ligand antibody having a heavy chain variable region of SEQ ID NO: 37 and a light chain variable region of SEQ ID NO: 38. An example of an antibody containing these variable regions is designated herein as IGF mAb_1.

In another embodiment, the IGF receptor antagonist is an IGF ligand antibody having a heavy chain variable region of SEQ ID NO: 41 and a light chain variable region of SEQ ID NO: 42.

In another embodiment, the IGF receptor antagonist is an IGF ligand antibody having a heavy chain variable region of SEQ ID NO: 43 and a light chain variable region of SEQ ID NO: 44.

In another embodiment, the IGF receptor antagonist is an IGF ligand antibody having a heavy chain of SEQ ID NO: 9, and a light chain of SEQ ID NO: 10.

In another embodiment, the IGF receptor antagonist is an IGF ligand antibody having a heavy chain of SEQ ID NO: 19, and a light chain of SEQ ID NO: 20.

In another embodiment, the IGF receptor antagonist is an IGF ligand antibody having a heavy chain of SEQ ID NO: 29, and a light chain of SEQ ID NO: 30.

In another preferred embodiment, the IGF receptor antagonist is an IGF ligand antibody having a heavy chain of SEQ ID NO: 39, and a light chain of SEQ ID NO: 40. An example of an antibody containing these heavy and light chains is designated herein as IGF mAb_1.

In another embodiment, the IGF receptor antagonist is an IGF receptor antibody having a heavy chain of SEQ ID NO: 45, and a light chain of SEQ ID NO: 46.

In another embodiment, the IGF receptor antagonist is figitumumab, dalotuzumab, cixutumumab, robatumumab, or ganitumab.

In another embodiment, the IGF receptor antagonist is linsitinib.

Preferably the IGF receptor antagonist is IGF mAb_1, as defined above. Manufacture and therapeutic use of the aforementioned antibodies is disclosed in WO2002/53596, WO2007/070432, WO2008/152422, WO2008/155387, and WO2010/066868.

In one embodiment, the antibody is produced by recombinant expression in a mammalian host cell, purified by a series of chromatographic and non-chromatographic steps, and formulated in an aqueous buffer composition for parenteral (intravenous) infusion or injection at an antibody concentration of 10 mg/ml, said buffer comprisingfor example 25 mM Na citrate pH 6, 115 mM NaCl, and 0.02% polysorbate 20. For intravenous infusion, the pharmaceutical composition may be diluted with a physiological solution, e.g. with 0.9% sodium chloride or G5 solution.

The antibody may be administered to the patient at a dose between 1 mg/kg to 20 mg/kg, by one or more separate administrations, or by continuous infusion, e.g. infusion over 1 hour. A typical treatment schedule usually involves administration of the antibody once every week to once every three weeks. For example, a weekly dose could be 5, 10, or 15 mg/kg. Preferably, the antibody is prepared at a concentration of 10 mg/ml of IGF mAb_1. The antibody may preferably be administered to a patient as a 750 mg (up to 1000 mg) total dose by one hour i.v. infusion, to be repeated once a week until disease progression The IGF receptor antagonist is administered to the patient in combination with administration of an androgen receptor antagonist. "In combination" means that both drugs are administered to the same patient within a certain time frame to achieve a therapeutic effect caused by the combined effects of both modes of action. In one aspect, the androgen receptor antagonist is administered on the same day as the IGF receptor antagonist. In another aspect of the invention, the androgen receptor antagonist is administered one, two, three, four, five, six or seven days before or after admistration of the IGF receptor antagonist.

In another embodiment, both active compounds are present within the same pharmaceutical composition. Hence, in another embodiment, the invention pertains to a pharmaceutical composition, comprising an IGF receptor antagonist and an androgen receptor antagonist, together with a pharmaceutically acceptable carrier.

An androgen receptor antagonist (AR antagonist) is a compound that blocks androgen receptor (AR) signaling. Androgen receptor antagonists prevent androgens from expressing their biological effects on responsive tissues. Such compounds may alter the androgen pathway by blocking the respective receptors, competing for binding sites on the receptor, affecting nuclear translocation, DNA binding of the receptor, or affecting androgen production. In the context of the present invention the androgen receptor antagonist can be an anti-androgen, an androgen synthesis inhibitor, a 17 α-hydroxylase/C17,20 lyase (CYP17A1) inhibitor, a 5-alpha-reductase inhibitor, a corticosteroid, a luteinizing hormone-releasing hormone (LH-RH) agonist, or an estrogen agonist.

In another embodiment, the androgen receptor antagonist is flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin, or estrogen.

In another embodiment, the androgen receptor antagonist is enzalutamide (Tran et al., Science 2009, 324(5928): 787-790.) Enzalutamide can be obtained from, for example, Medivation or Astellas under the name Xtandi®. Enzalutamide is preferably administered as a dosage of 160 mg once daily during each cycle of treatment In another embodiment, the androgen receptor antagonist is abiraterone, for example in the form of abiraterone acetate (Agarwal et al., Future Oncology 2010, 6(5): 665-679). Abieraterone can be obtained from, for example, Janssen Biotech, Inc.

Manufacture, formulation, and use of the androgen receptor antagonist depends on the actual compound chosen and can be found in the state of the art.

Another embodiment of the invention is an androgen receptor antagonist for use in the treatment of prostate cancer in combination with an IGF receptor antagonist. In another embodiment the use of an androgen receptor antagonist in combination with an IGF receptor antagonist is for the treatment of benign prostatic hyperplasia. In a further embodiment, said androgen receptor antagonist is flutamide, nilutamide, enzalutamide, bicalutamide, ketonazole, abiraterone acetate, orteronel, finasteride, dutasteride, bexlosteride, izonsteride, turosteride, episteride, dexamethasone, prednisone, leuprolide, goserelin, triptorelin, histrelin, or estrogen.

Another embodiment of the invention pertains to a method of treatment of prostate neoplasia comprising administering a therapeutically effective amount of an IGF receptor antagonist to a patient in need thereof, and additionally administering a therapeutically effective amount of an androgen receptor antagonist to the same patient on the same day, or one, two, three, four, five, six or seven days before or after admistration of the IGF receptor antagonist.

By "prostate neoplasia", this aspect of the invention include where the prostate neoplasia is prostate cancer, including benign and malignant tumours, and particularly castration resistant prostate cancer; and also benign prostatic hyperplasia.

A "therapeutically effective amount" of the IGF or androgen receptor antagonist to be administered is the minimum amount necessary to prevent, ameliorate, or treat a prostate neoplasia, in particular castration-resistant prostate cancer, or benign prostatic hyperplasia.

In another embodiment, the invention pertains to the use of an IGF receptor antagonist for the manufacture of a medicament for the treatment of prostate neoplasia, wherein the IGF receptor antagonist is to be used in combination with an androgen receptor antagonist.

By "prostate neoplasia", this aspect of the invention include where the prostate neoplasia is prostate cancer, including benign and malignant tumours, and particularly castration resistant prostate cancer; and also benign prostatic hyperplasia.

In another embodiment, the invention pertains to the use of an androgen receptor antagonist for the manufacture of a medicament for the treatment of prostate cancer neoplasia, wherein the androgen receptor antagonist is to be used in combination with an IGF receptor antagonist.

By "prostate neoplasia", this aspect of the invention include where the prostate neoplasia is prostate cancer, including benign and malignant tumours, and particularly castration resistant prostate cancer; and also benign prostatic hyperplasia.

EXAMPLES

Materials and Methods

Compounds

IGF mAb_1 is an antibody against IGF ligand having a heavy chain of SEQ ID NO: 39 and a light chain of SEQ ID NO: 40. Its manufacture has been disclosed in WO 2010/066868.

IGF mAb_2 is an antibody against IGF ligand having a heavy chain of SEQ ID NO: 29 and a light chain of SEQ ID NO: 30. Its manufacture has been disclosed in WO 2010/066868.

Cell Culture

DU-145 (ATCC, HTB-81), BM-1604 (DSMZ, ACC 298), PC-3 (ATCC, CRL-1435), 22Rv1 (ATCC, CRL-2505), LNCaP (ATCC, CRL-1740), and DUCaP cells (generated in the lab of Prof K J. Pienta, Hallym University, College of Medicine, Seoul, Korea; Lee Y G et al., In Vivo 2001; 15(2):157-62) were cultivated in RPMI 1640 growth medium (GIBCO, #31870) supplemented with 10% heat inactivated fetal calf serum (FCS; JRH, #12103), and 2 mM L-glutamine (GIBCO, #25030); NCI-H660 (ATCC, CRL-5813) were grown in RPMI supplemented with 5% FCS, 4 mM L-glutamine, 5 µg/ml insulin, 0.01 mg/mL transferrin, 30 nM sodium selenite, 10 nM beta estradiol and 10 nM hydrocortisone. C4-2 and C4-2b (both licensed from MD Anderson Cancer Center; Thalmann G N et al., Cancer Res. 1994; 54:2577-2581) and VCaP (ATCC, CRL-2876) were cultivated in DMEM (Lonza, #12-604F) supplemented with 10% heat inactivated FCS, 2 mM L-glutamine and R1881 (Sigma, #R0908; VCaP with 0.1 nM and C4-2/C4-2b with 1 nM). MDA-PCa-2b (ATCC, CRL-2422) were grown in F-12K (GIBCO, #21127) supplemented with 20% heat-inactivated FCS, 25 ng/ml cholera toxin, 0.005 mM ethanolamine, 100 µg/ml hydrocortisone, and 45 nM selenious acid. Bob cells (ECACC, #10021102) were cultured in keratinocyte-SFM (Invitrogen, #37010-022) supplemented with prequalified human recombinant epidermal growth factor 1-53, bovine pituitary extract and glutamine, 2 ng/ml leukemia inhibitory factor, 2 ng/ml stem cell factor, 100 ng/ml cholera toxin, and 1 ng/ml granulocyte macrophage colony stimulating factor. Shmac 4 (ECACC, #10112302), Shmac 5 (ECACC, #10112303) and P4E6 cells (ECACC, #10112301) were grown in Stemline Keratinocyte Medium II (Sigma, #S0196) with Stemline Keratinocyte Growth Supplement (Sigma, #S9945), 2 mM L-glutamine and 2% FCS. The cells were maintained in 75 cm$^2$ tissue culture flasks (Nunc, #178905) at 37° C. in 5% $CO_2$ in a humidified atmosphere.

2D Cell Proliferation Assay

The following method was used to determine the inhibitory effect of IGF ligand-neutralizing mAbs and androgen signaling inhibitors on the growth of prostate cancer cell lines. Assays were performed in cell growth medium containing 10% serum.

Adherent cells were detached with trypsin/EDTA solution (GIBCO, #043-9031 FU), resuspended in growth medium, centrifuged, resuspended in assay medium (supplemented with 10% heat inactivated FCS and 2 mM L-glutamine) and diluted to 5,000-40,000 cells per mL. 100 µL/well cell suspension was added to each well of a sterile flat-bottom white 96-well plate (PerkinElmer, #6005280) and plates were incubated overnight in a humidified incubator set at +37° C. and 5% $CO_2$. On the next day supernatants were aspirated and 35 µL/well assay medium was added to all wells.

Serial dilutions of IGF mAb_1 and mAb_2 (1 µM highest concentration), MDV-3100 (10 µM highest concentration), abiraterone acetate (100 µM highest concentration) were prepared on a separate plate in assay medium (no growth factors or hormones supplemented). All agents were tested as single agents or in combination. All samples were tested in triplicate wells (100 µL/well assay). Plates were incubated for 5 days in a humidified incubator at +37° C. and 5% $CO_2$. After this incubation period, CellTiter-Glo buffer, substrate and test plates were equilibrated to RT. CellTiter-Glo is a bioluminescent assay (Promega, #G7571) designed to determine the number of viable cells in culture, in which the generation of a luminescent signal is proportional to the amount of ATP present in cells. 100 µL of freshly mixed CellTiter-Glo reagent was added to each well. After 2 min on an orbital shaker (MTS 2/4, IKA) and 10 min incubation at RT, luminescence was recorded (luminescence reader (Genios Pro, Tecan or Victor X4, Perkin Elmer), integration time 1 sec).

Generation of Cell Lysates and Immunoblotting

One×$10^6$ and 4×$10^6$ cells were plated in 6-well plates and 10 cm dishes, respectively, in medium containing 10% heat-inactivated FCS and after over night incubation the cells were treated with 1 µM of MDV-3100 and 100 nM of IGF mAb_1 or a combination of antibody and AR signaling inhibitor. After 24 hours the cells were lyzed on the plates, total protein was isolated and protein concentration was determined by Bradford assay. Cell lysates were snap frozen and stored at −80° C.

Western blotting was performed loading 30-50 µg of total protein lysates on a 4-12% Bis-Tris PAG (Bio Rad) and blotting with the Bio Rad trans-Blot® Turbo system using a PVDF membrane. Membranes were incubated over night at 4° C. with antibodies against the following proteins: IGF-1R beta (#3027, Cell Signaling; 1:1000), p-5473 AKT (#4060, Cell Signaling; 1:2000), AKT (#9272, Cell Signaling; 1:1000), PTEN (#9559, Cell Signaling; 1:1000), AR (N-20, # sc-816, Santa Cruz; 1:200), and GAPDH (#7298, Cell Signaling; 1:1000)(which served as loading control). Cell cycle regulators and markers of proliferation and apoptosis were analyzed using the following antibodies: p21 Waf1/Cip1 (12D1; #2947, Cell Signaling; 1:1000), CDK2 (78B2; #2546, Cell Signaling; 1:1000), Cyclin E (C-19; sc-198, Santa Cruz; 1:1000), PCNA (#2586, Cell Signaling; 1:2000), and PARP (#9542, Cell Signaling; 1:1000).

Antibody dilutions were prepared in 5% BSA or 5% non-fat dry milk in TBS-0.5% Tween20 (TBS-T). Following washes in TBS-T membranes were incubated with a polyclonal HRP-conjugated goat anti-rabbit secondary antibody (DAKO, #P0448) for 1 hour and after further washes in TBS-T antibody reactivity was detected by means of ECL/Super ECL (GE Healthcare) and exposure on ImageQuant LAS4000. For the detection of total protein levels, membranes incubated with anti-phospho antibodies were stripped in Restore Western Blot Stripping Buffer (Thermo, #21059) for 15-20 min, blocked, and incubated with the antibody against the total protein before the membrane was processed as described above.

Cell Cycle Analysis Using Flow Cytometry

4×$10^5$ VCaP cells were treated with 1 µM of IGF mAb_1 and 10 µM of MDV-3100, and the combination of both agents, and incubated in 6-well plates at 37° C. for 24 h, 48 h and 72 h. Subsequently, the supernatant was transferred to FACS tubes, adherent cells were detached with trypsin and collected in the respective FACS tubes. After centrifugation, the medium was discarded and the cell pellet was fixed in ice-cold 70% ethanol for a minimum of 2 h at 4° C. After removing the ethanol entirely, fixed cells were stained with propidium iodide (10 µg/ml; Sigma; P4864-10 mL) in a hypotonic buffer solution (0.1% sodium citrate, 0.1% (v/v) triton X-100, 100 µg/ml DNase-free RNase A) and incubated in the dark at room temperature for 30 minutes. Cells were analyzed using the Becton Dickinson FACS Canto II Flow cytometer and data was evaluated with the FACS Diva software.

Thymidine Incorporation Assay

VCaP cells were treated with 1 µM of IGF mAb_1 and 10 µM of MDV-3100 and the combination of both agents and incubated as triplicates in flat-bottom 96-well plates for 96 hours at a density of $5 \times 10^4$ cells per well, in the absence of R1881. For the last 24 hours of incubation, $^3$H-thymidine (0.4 µCi/well; PerkinElmer, NET355001 MC) was added. Afterwards, the plates were frozen and incubated at –20° C. for 24 h. For harvesting, the plates were thawed and 40 µL Trypsin was added to each well to detach the cell fragments. The suspension was transferred to filter plates. The plates were then washed three times with distilled water and dried at 60° C. for 3 h. 25 µL per well Microscint were added and the proliferation rate was determined by measuring thymidine incorporation (CPM; counts per minute) using a liquid scintillation counter (1450 Microbeta Wallac Trilux, Perkin-Elmer).

Analysis of Cellular Doubling Time $3 \times 10^5$ cells/well VCaP cells were seeded in 2 mL cell culture medium per well. 24 hrs post seeding the cell culture medium was removed and replaced with DMEM+10% FCS without R1881. 24 hr following the medium change the pre-treatment wells were harvested and counted with the Beckman Coulter™ Vi-CELL XR 2.03, and 10 µM of MDV-3100 was added to the remaining cells. Four times every 24 hr VCaP cell number was determined in 3 wells for each time point. The mean value was calculated from these triplicates. To determine the generation time, following formula is used:

$$[h]\text{generation time} = \frac{\log 2 \times \text{cultivation hours } [h]}{\log N - \log No}$$

$$[h]\text{generation time} = \frac{\log 2 \times \text{cultivation hours } [h]}{\log N - \log No}$$

$No$ = cell count at $T0$ $N$ = cell count after cultivation

Assessment of Caspase 3 Activity

To acquire live cell images of cells undergoing caspase-3/7 mediated apoptosis upon treatment with different concentrations of MDV-3100, IGF mAb_1, and the combination of both agents, the CellPlayer™ 96-Well Kinetic Caspase-3/7 Reagent (Essen BioScience; #4440) was used. 50000 VCaP cells/100 µl/well were seeded and treated on the next day with the respective concentrations of both agents in growth medium in the absence of R1881. The Caspase-3/7 reagent was diluted to a final concentration of 5 µM in 100 µl per well of growth medium and added to the medium. The plate was placed within a microplate tray into the IncuCyte™ 2011A and 3 images per well were acquired every 4 hours for 7 days using the phase contrast and fluorescence channels.

Example 1

Inhibitory Effect of IGF and AR Signaling Blockade on Prostate Cancer Cell Proliferation In order to test the anti-proliferative effects of the combination of AR and IGF-1/2 inhibition, 10 different prostate cancer cell lines (Bob, C4-2, C-4-2B, DUCaP, MDA PCa 2b, P4E6, PC-3, Shmac 4, Shmac 5, VCaP) were treated with the AR antagonist MDV-3100 and fully human monoclonal antibodies against the IGF ligands (IGF mAb_1 and IGF mAb_2), as single agents and in combination, in 2D cell proliferation assays (Table 1). Three of the tested cell lines (VCaP and DUCaP—both cell lines were derived from the same prostate cancer patient from different sites of metastasis, and MDA PCa 2b) showed single agent anti-proliferative response to both the AR and IGF signaling inhibition alone, and an enhanced effect when combined (FIG. 1).

Example 2

Inhibitory Effect of IGF Signaling and Androgen Synthesis Blockade on Prostate Cancer Cell Proliferation As a second approach to test the combination potential of androgen and IGF signaling inhibition, 8 different prostate cancer cell lines (22Rv1, BM 1604, DU-145, DUCaP, LNCaP, MDA PCa 2b, PC-3, VCaP) were treated with abiraterone acetate, which selectively inhibits CYP17A and thus de novo synthesis of androgens, alone and in combination with IGF-ligand neutralizing monoclonal antibodies (IGF mAb_1 and IGF mAb_2). The results from these assays also identified VCaP, MDA PCa 2b, and DUCaP cells to be the only cell lines which are responsive to both single agent and combination treatments. Treatment with abiraterone acetate, however, implies autocrine androgen production by the tumor cells for abiraterone acetate to show anti-proliferative effects. This might limit the number of cells sensitive to abiraterone acetate treatment. Results of 2D and 3D proliferation assays for VCaP and 2D assays of MDA PCa 2b and DUCaP cells are shown in FIG. 2. These data suggest that the single agent effects of abiraterone acetate on cell proliferation can be enhanced by the combination with antibodies neutralizing IGF ligands.

Example 3

Figure 1A:
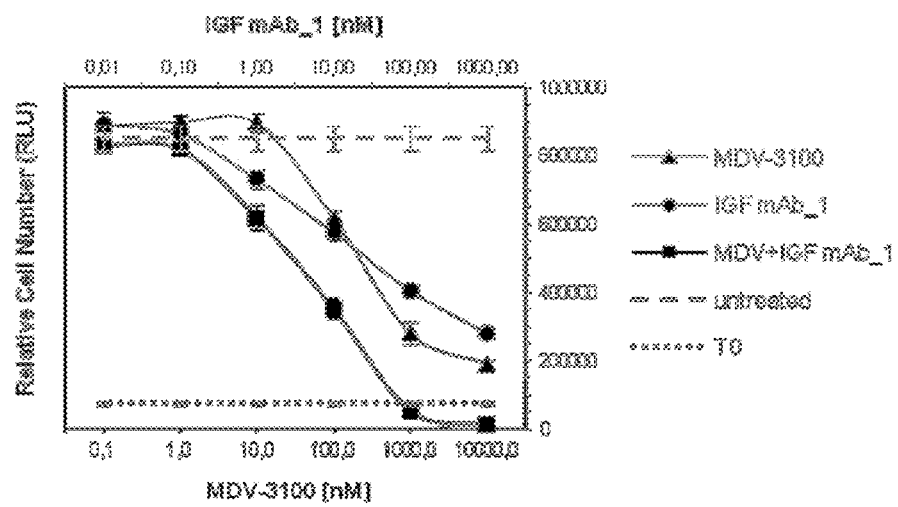
FIG. 1A-F. Inhibitory effect of IGF and AR signaling blockade on VCaP, MDA PCa 2b and DUCaP cell proliferation VCaP, MDA PCa 2b and DUCaP cells were treated with MDV-3100 and IGF ligand-neutralizing antibodies as single agents and in combination.
Figure 1B:
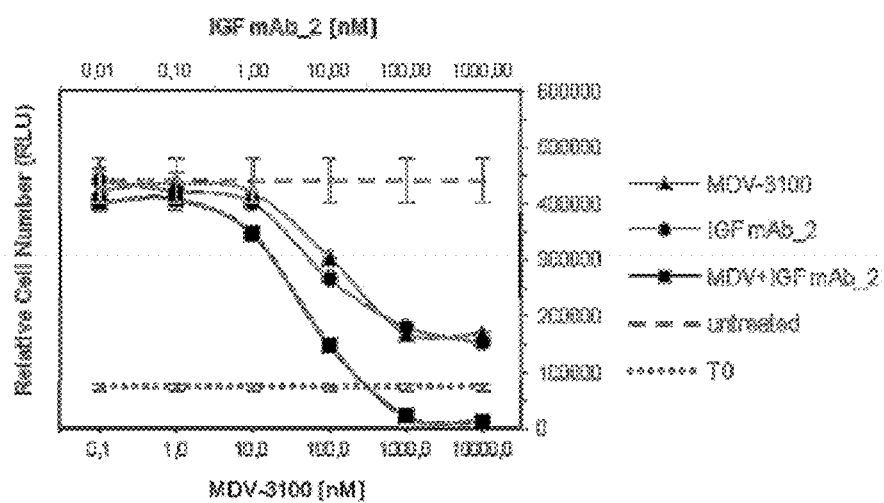
Figure 1C:
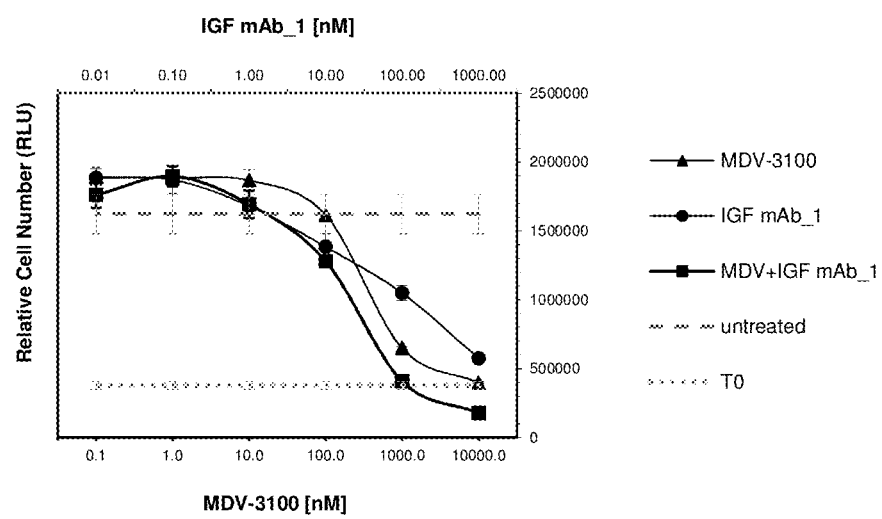
Figure 1D:
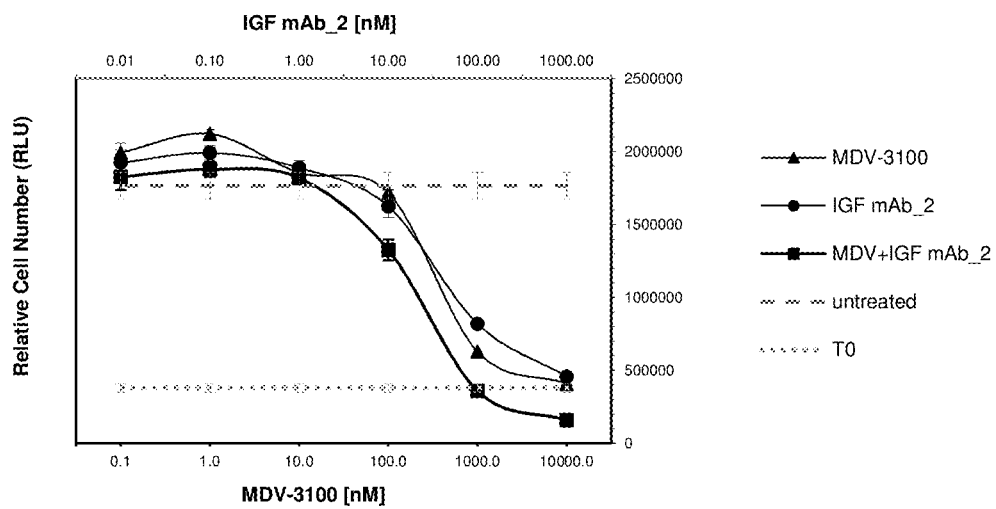
Figure 1E:
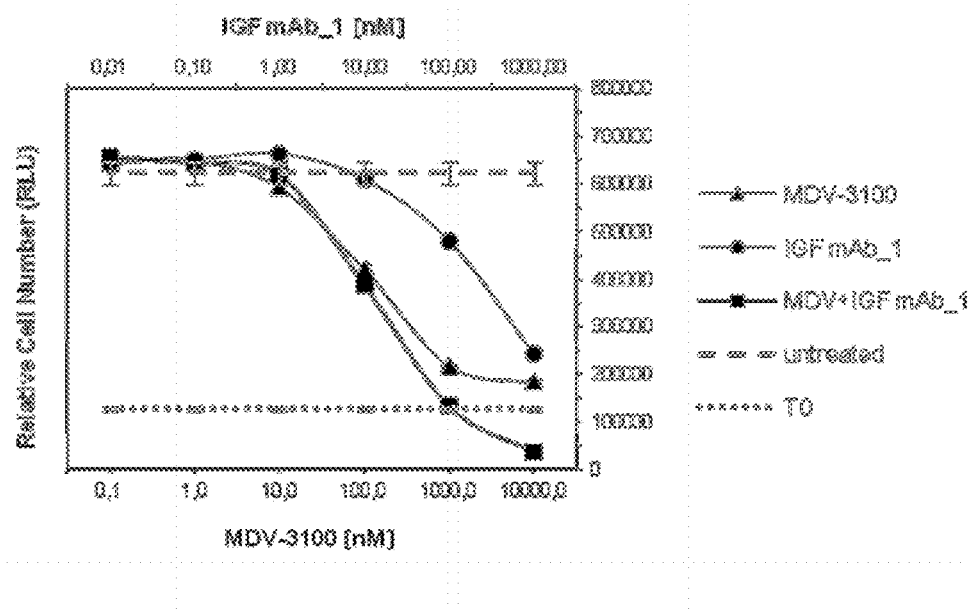
Figure 1F:
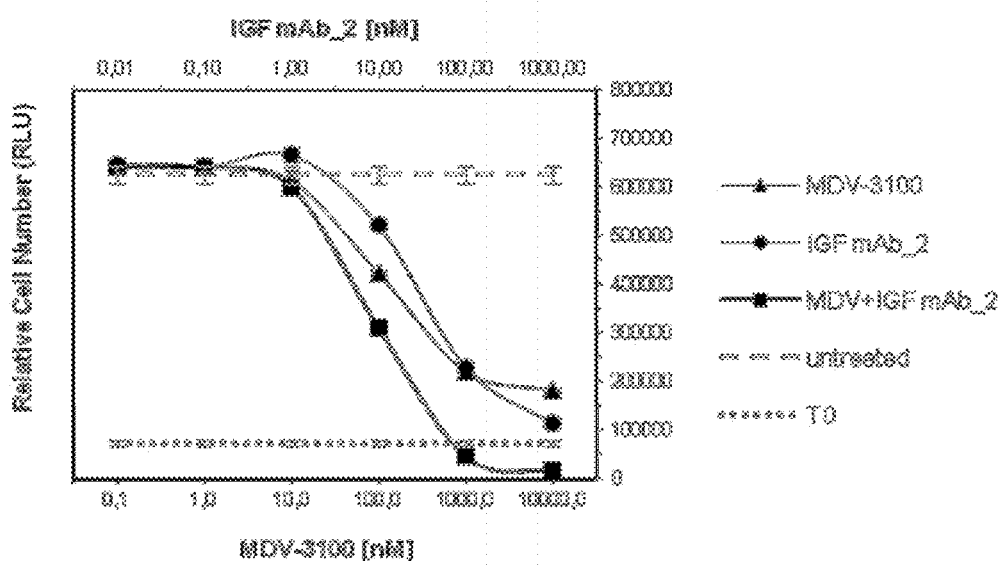
Figure 2A:
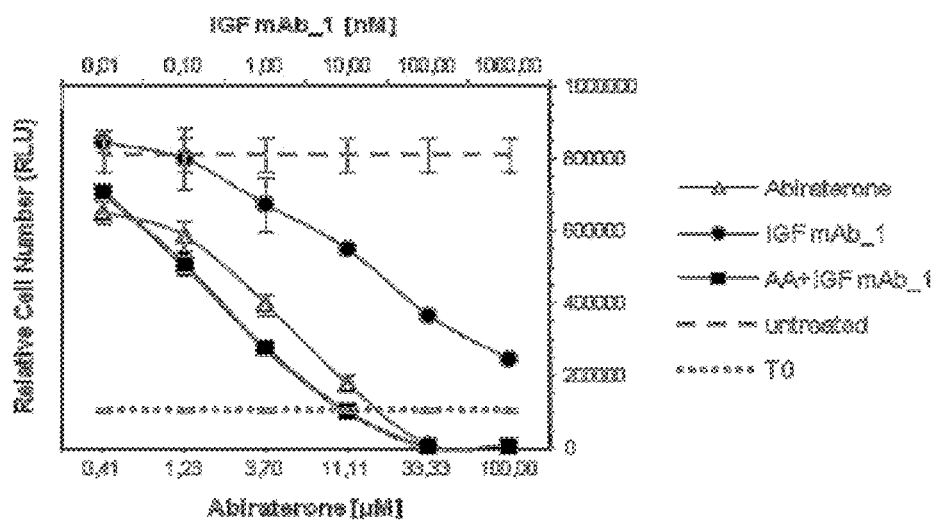
FIG. 2A-G. Inhibitory effect of IGF signaling and androgen synthesis blockade on VCaP, MDA PCa 2b and DUCaP cell proliferation FIGS. 2A-G demonstrate the effects of the IGF mAb_1 and IGF mAb_2 antibodies and abiraterone acetate (AA), as single agents and in combination, on the 2D and 3D proliferation of prostate cancer-derived VCaP, MDA PCa 2b, and DUCaP cells in 10% FCS-containing growth medium.
Figure 2B:
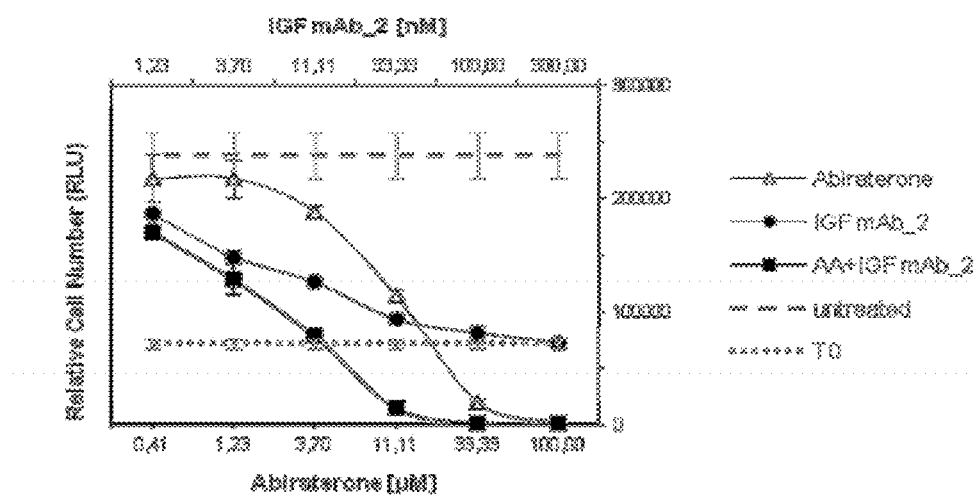
Figure 2C:
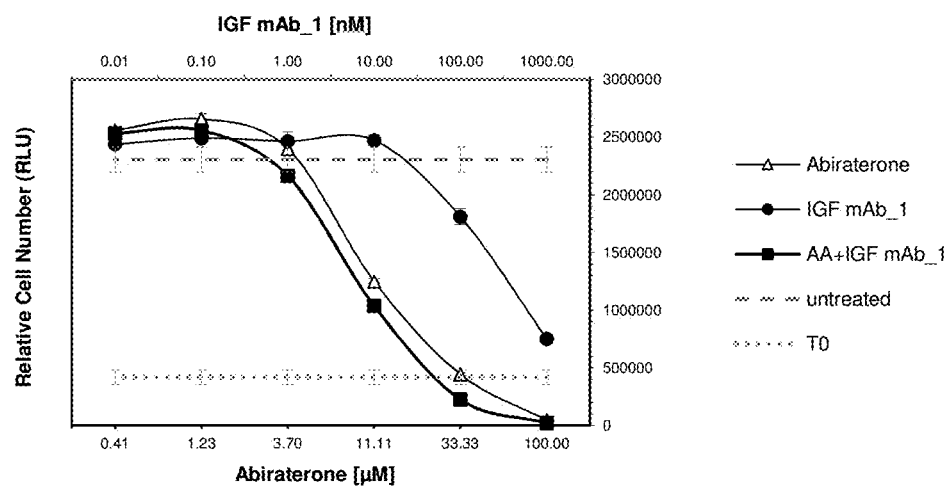
Figure 2D:
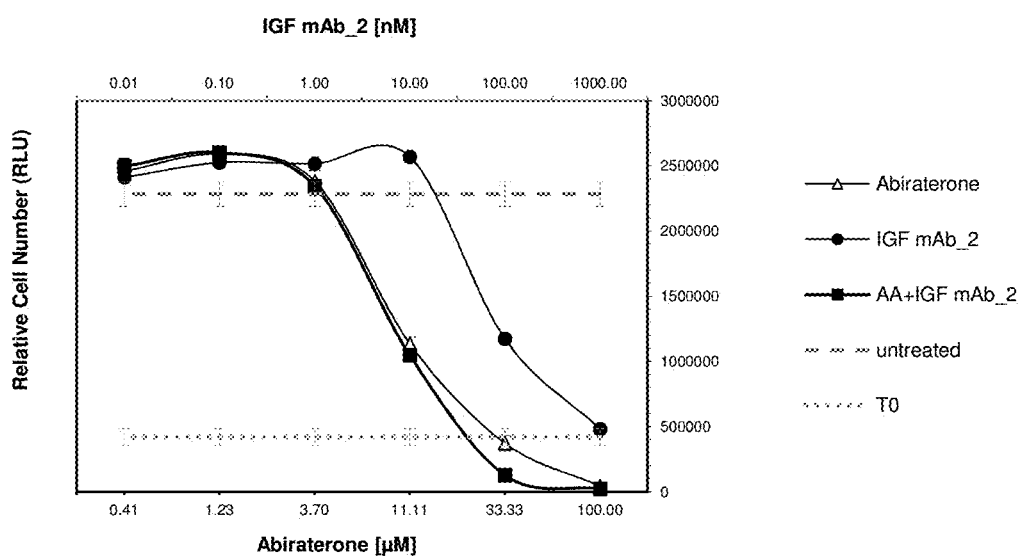
Figure 2E:
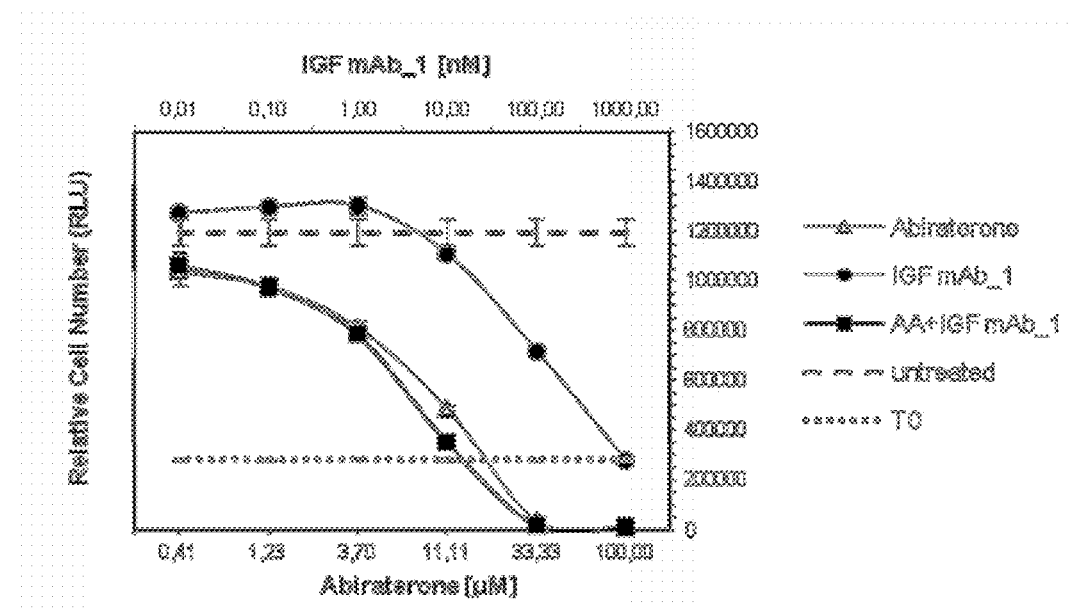
Figure 2F:
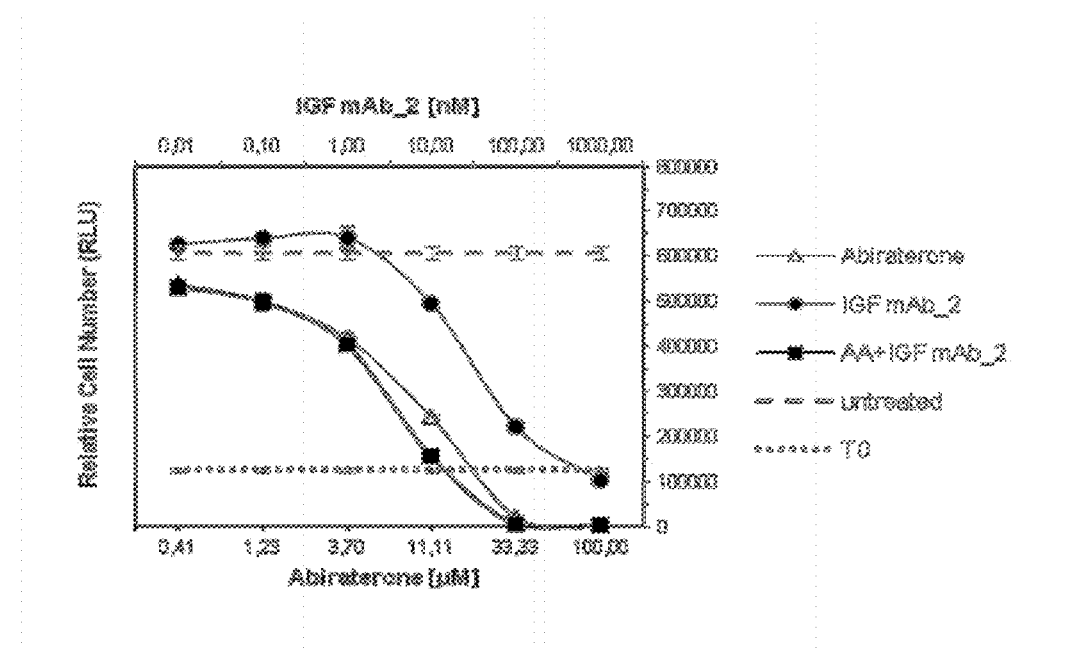
Figure 2G:
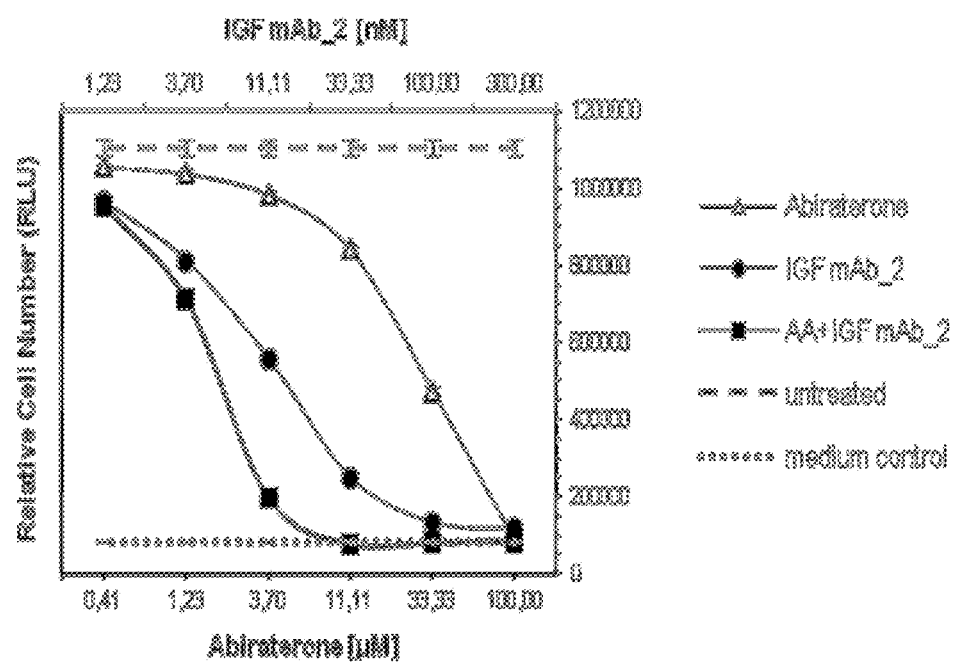
Figure 3A:
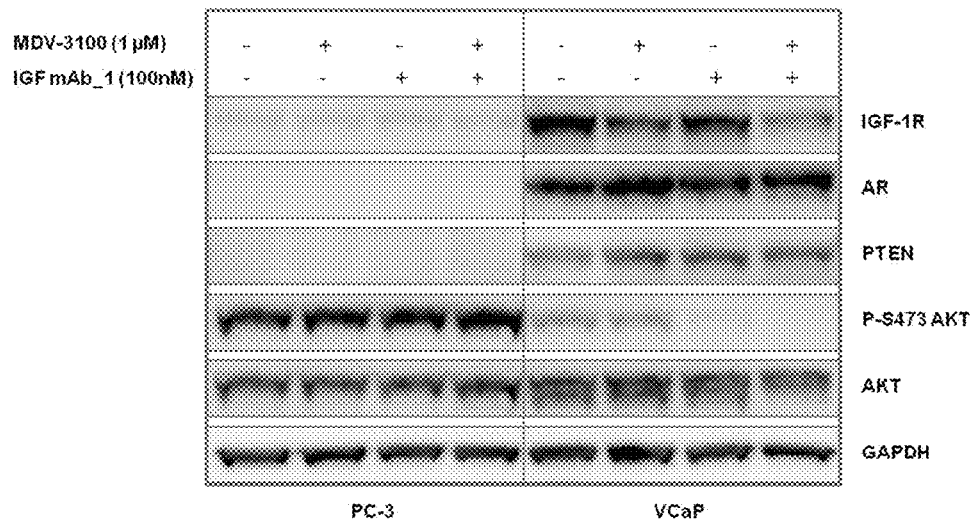
FIG. 3A-C. Protein analysis in VCaP, MDA PCa 2b and DUCaP cells following IGF and AR signaling inhibition
Figure 3B:
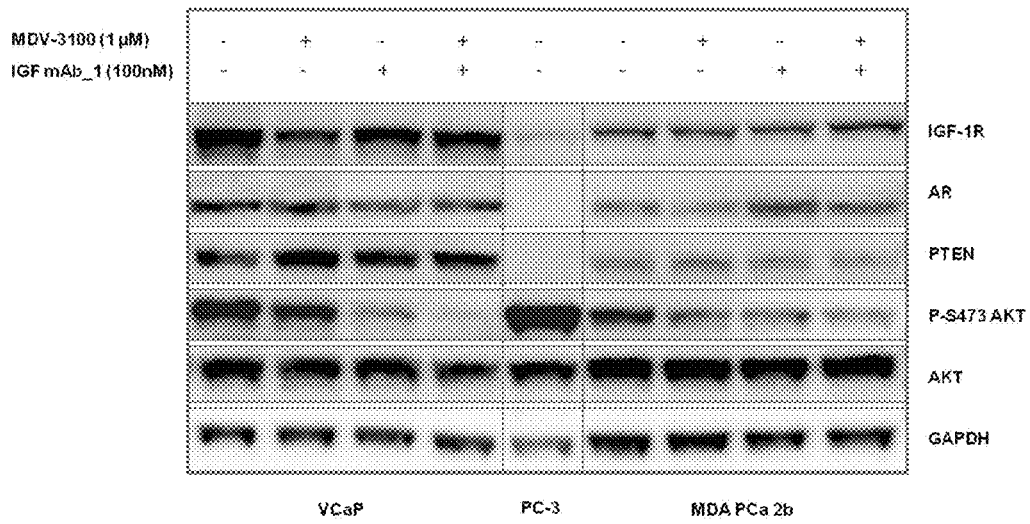
Figure 3C:
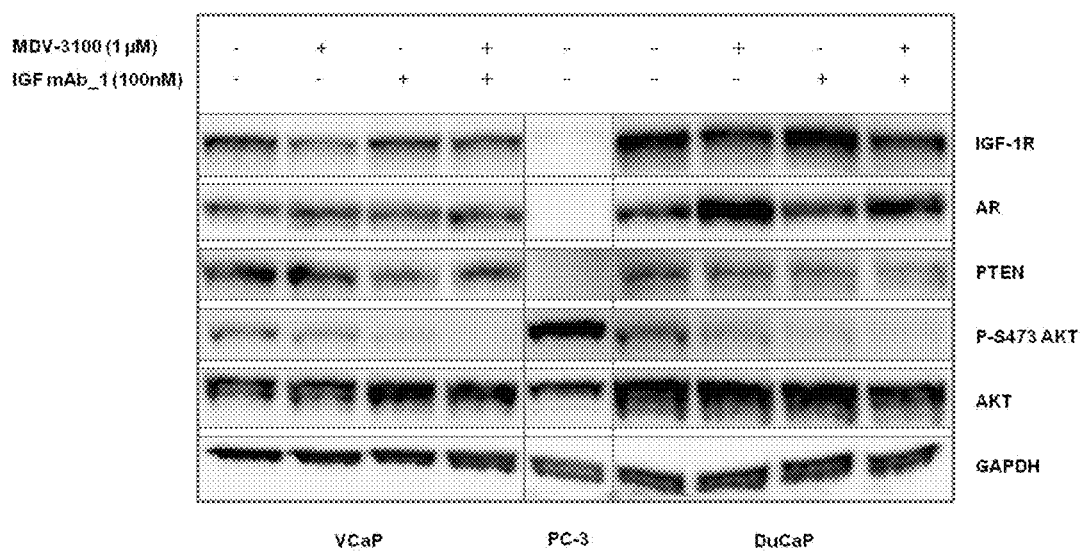

The Presence of Androgen Receptor and IGF-1R as Well as Expression of PTEN and Wt PIK3CA Characterizes Prostate Cancer Cells Sensitive to the Combination of Androgen and IGF Signaling Inhibitors FIG. 3 shows signaling protein expression in the VCaP, MDA PCa 2b, and DUCaP cell lines, which are sensitive to AR and IGF signaling inhibition, in comparison to the insensitive cell line PC-3. Cells were treated with MDV-3100 and IGF mAb_1 as single agents, or in combination, for 24 hours and protein lysates were compared to untreated controls for protein expression of IGF-1R, AR, PTEN and AKT, and for phosphorylation of AKT-Ser473. Responsive cell lines expressed wt AR, IGF-1R, and PTEN. These characteristics were not present in PC-3 or the other tested cell lines which did not show an anti-proliferative responce to either one of the single agent treatments or the combination of both agents (Table 1).

These results indicate that in the presence of androgen receptor, IGF-1R, and expression of PTEN (and wt PIK3CA), the combination of androgen and IGF signaling inhibitors results in an increased efficacy in blocking prostate cancer cell proliferation in vitro.

Example 4

Prolonged AKT Phosphorylation Inhibition Following Combined Treatment of MDV-3100 and IGF mAb_1

Figure 4:
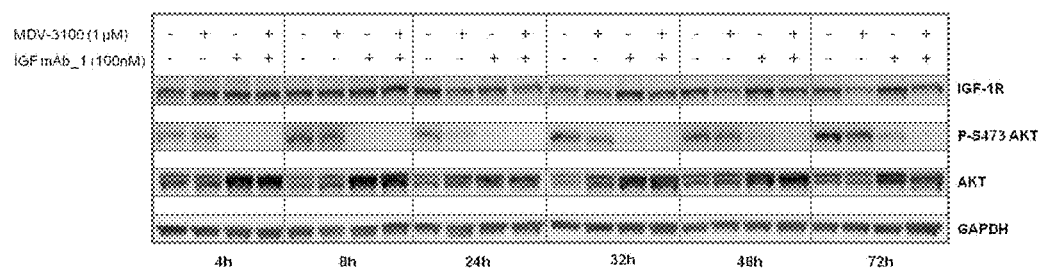
FIG. 4. IGF signaling pathway inhibition following single agent and combination treatment of IGF mAb_1 and MDV-3100.

The effects of MDV-3100 and IGF ligand mAb (IGF mAb_1) as single agents, and combined treatment, on the inhibition of AKT phosphorylation were analyzed by Western blot from 4 h until 120 h of treatment. The combination of both agents resulted in a more complete and longer lasting inhibition of AKT phosphorylation than the antibody treatment alone (FIG. 4).

Example 5

Figure 5:
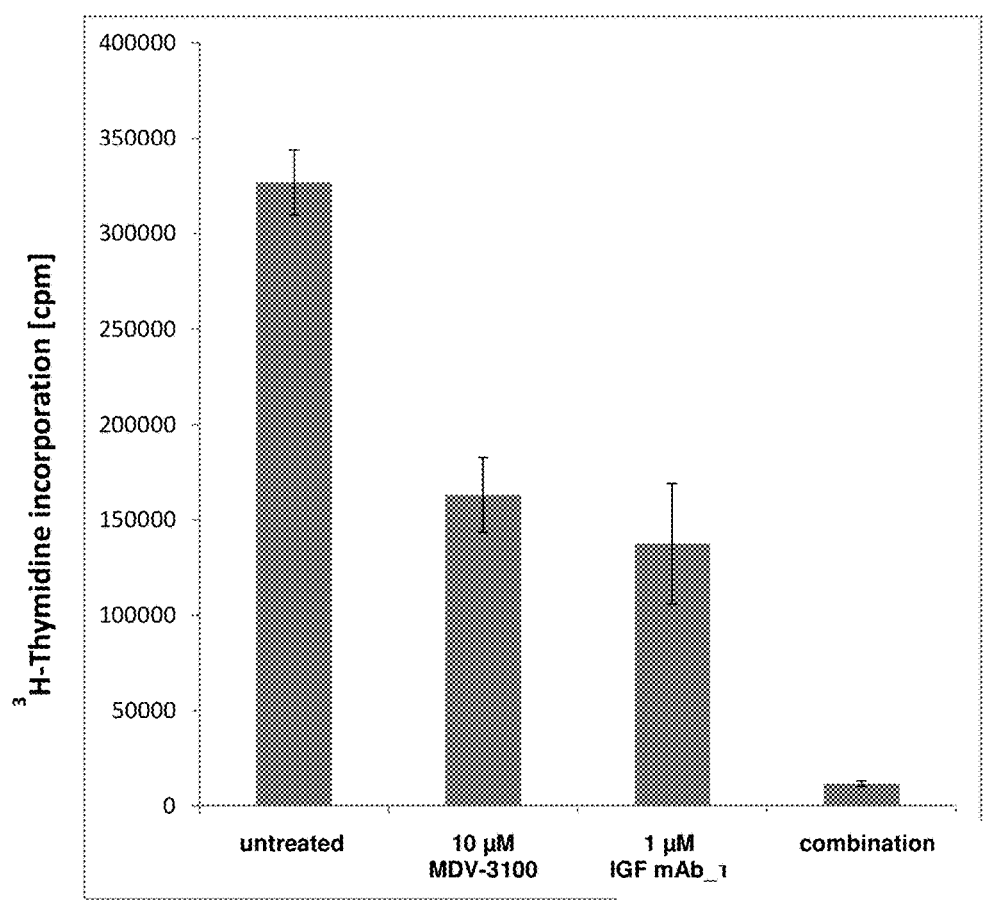
FIG. 5. Reduced proliferative activity of VCaP cells following single agent and combination treatment of IGF mAb_1 and MDV-3100

Combined Treatment with IGF mAb_1 and MDV-3100 Leads to a Synergistic Effect on Apoptotic Induction in VCaP Cells In support of the data shown in FIG. 1, results from tritiated thymidine incorporation assays shown in FIG. 5 demonstrates that both MDV-3100 and IGF mAb_1 alone have an inhibitory effect on cell proliferation (approximately 50%), however, the combination of both agents was much more effective. Treatment of VCaP cells with IGF mAb_1 alone led to a modest increase in apoptosis as assessed by phase contrast microscopy (FIG. 6A), caspase 3 activity (FIG. 7), FACS-based cell cycle analysis (FIG. 8), and PARP cleavage (FIG. 9). In contrast, the reduced cell number seen after treatment with MDV-3100 alone (FIG. 6A) was due to prolonged cellular doubling time (FIG. 6B). MDV-3100 did not induce caspase 3 activity (FIG. 7), sub-G1 apoptosis cell population (FIG. 8), or PARP cleavage (FIG. 9). However, when IGF mAb_1 and MDV-3100 were combined a synergistic effect on caspase 3 activity was observed (FIG. 7), in addition to enhanced sub-G1 apoptotic cell population (FIG. 8) and cleaved PARP (FIG. 9).

Example 6

Proposed Study of IGF mAb_1 in Combination with Enzalutamide

Introduction

The study proposed here investigates the safety and anti-tumour activity of IGF mAb_1 in combination with enzalutamide, compared to enzalutamide given alone, in CRPC patients This randomised, open label, study will be conducted to explore the anti-tumour activity and safety profile of the combination of IGF mAb_1 and enzalutamide (Arm A), compared to enzalutamide (Arm B). A tolerability and safety phase Ib will be performed to determine the maximum tolerated dose (MTD), and/or recommended phase II dose, in addition to any safety issues before commencement of the randomised trial.

IGF mAb_1 will be administered weekly in 28 day cycles of treatment by a one hour intravenous infusion at the start of each treatment cycle. Enzalutamide will be administered daily by continuous oral dosing during each treatment cycle.

Background

IGF mAb_1 is a fully human monoclonal antibody (HumAb) of the IgG1 isotype. The Ab binds with high affinity to IGF-1 and IGF-2, and potently neutralizes the proliferative and prosurvival cellular signaling triggered by both proteins.

Enzalutamide is an androgen receptor antagonist that acts on different steps in the androgen receptor signalling pathway. The chemical name is 4-{3-[4-cyano-3-(trifluoromethyl)phenyl]-5,5-dimethyl-4-oxo-2-sulfanylideneimidazolidin-1-yl}-2-fluoro-N-methylbenzamide. The molecular weight is 464.44 and molecular formula is $C_{21}H_{16}F_4N_4O_2S$. Enzalutamide is indicated for the treatment of patients with metastatic castration-resistant prostate cancer (CRPC)

Administration

IGF mAb_1 will be administered weekly in 28 day cycles of treatment, by a one hour intravenous infusion at the start of each treatment cycle. Enzalutamide will be administered daily by continuous oral dosing during each treatment cycle.

Selection of Trial Population

A total of up to approximately 140 patients may be recruited into the study. Approximately 15-18 patients will be entered into the part I tolerability and safety phase of the study to ensure the safety of the combination therapy and determine the part II recommended dose. In part II of the study, 120 patients will be randomised onto one of the two study arms, with 60 patients randomised to each arm (Arm B=60, Arm B=60).

Part I of the study will be performed in 3 or more centres. Part II of the study will be performed in 10 or more centres globally.

A log of all patients included into the study (i.e. having given informed consent) will be maintained in the ISF at the investigational site irrespective of whether they have been treated with investigational drug or not.

Main Diagnosis for Study Entry

Patients to be included in this study must have diagnosed and histologically, or cytologically, confirmed metastatic CRPC and have received and progressed after one line of docetaxol treatment. Patients may, or may not, have received and failed prior abiraterone, or cabazitaxel treatment, in any setting.

Inclusion Criteria

1. The patient has histologically, or cytologically, confirmed adenocarcinoma of the prostate.
2. Male patient aged 18 years old.
3. Patients with radiographic evidence of metastatic prostate cancer (stage M1 or D2). Distant metastases evaluable by radionuclide bone scan, CT scan, or MRI within 28 days of start of study treatment.
4. Patients who have disease progression (biochemical, clinical or radiographic) while receiving docetaxel, or within 120 days of completing docetaxel-based chemotherapy and in the opinion of the investigator is unlikely to derive significant benefit from additional docetaxel-based therapy, or was intolerant to therapy with this agent.
5. Patients must have evidence of progressive disease defined as at least one of the following:
    a. Progressive measurable disease: using conventional solid tumour criteria RECIST 1.1.
    b. Bone scan progression: at least two new lesions on bone scan.
    c. Increasing PSA: at least two consecutive rising PSA values over a reference value (PSA #1) taken at least 1 week apart. A third PSA (PSA #3) is required to be greater than PSA #2; if not, a fourth PSA (PSA #4) is required to be greater than PSA #2.
6. Patients with a PSA 2 ng/mL.

7. Patients with prior surgical or medical castration with a serum testosterone of <50 ng/mL. If the method of castration is luteinizing hormone releasing level hormone (LHRH) agonists, the patient must be willing to continue the use of LHRH agonists during protocol treatment.
8. Eastern Cooperative Oncology Group performance status (ECOG PS) 0, 1 or 2.
9. Patients have adequate hematologic function (absolute neutrophil count [ANC]≥1500/uL, hemoglobin≥9/dL, and platelets≥100,000/uL).
10. Patients have adequate hepatic function (bilirubin≤1.5 times the upper limit of normal (ULN)], aspartate transaminase [AST] and alanine transaminase [ALT]≤3 times the ULN, or ≤5 times the ULN if liver metastases are present).
11. Adequate renal function (creatinine≤1.5×ULN or calculated creatinine clearance>40 mL/min).
12. A urinary protein of ≤1+ on dipstick or routine urinalysis (UA). If urine dipstick or routine analysis indicates ≥2+ proteinuria, then a 24-hour urine must be collected and must demonstrate <1000 mg of protein in 24 hours to allow participation in the study.
13. Adequate coagulation function (an international normalized ratio [INR]≤1.5 and a partial thromboplastin time [PTT]≤5 seconds above the ULN [unless on oral anticoagulant therapy]). Patients receiving full-dose anticoagulation therapy are eligible provided they meet all other criteria, are on a stable dose of oral anticoagulant or low molecular weight heparin (except warfarin, which is not permitted).
14. Fasting plasma glucose <8.9 mmol/L (<160 mg/dL) or HbA1c<8.0%.

Exclusion Criteria
1. Patients that have received more than two prior taxane based cytotoxic chemotherapy regimen for metastatic disease. Patients who have had a treatment break from docetaxol followed by a second or third docetaxel-based regimen, with subsequent disease progression, are eligible.
2. Patients that have received prior enzalutamide in any setting will not be eligible.
3. Patients who have received abiraterone, or cabazitaxel treatment, within 4 weeks before start of study treatment.
4. Patient that have received prior therapy with mitoxantrone for advanced prostate cancer (prior adjuvant therapy with mitoxantrone is permitted).
5. Patients that have been treated with any of the following within 4 weeks of starting trial medication: chemotherapy, immunotherapy, biological therapies, molecular targeted, hormone therapy, radiotherapy (except in case of localized radiotherapy for analgesic purpose or for lytic lesions at risk of fracture which can then be completed within 2 weeks prior to study treatment).
6. Use of any investigational drug within 4 weeks before start of trial treatment or concomitantly with this trial.
7. Patients that have been treated with strong CYP2C8 inhibitors; strong or moderate CYP3A4 or CYP2C8 inducers; CYP3A4, CYP2C9 and CYP2C19 substrates with a narrow therapeutic index, within 4 weeks of starting the trial.
8. Patients with a history of symptomatic congestive heart failure or has a pre-study echocardiogram or multigated acquisition (MUGA) scan with left ventricular ejection fraction (LVEF) that is ≥10% below the LLN.
9. QTcF prolongation >450 ms or QT prolongation deemed clinically relevant by the investigator (e.g., congenital long QT syndrome). The QTcF will be calculated as the mean of the 3 ECGs taken at screening.
10. Patients with small cell or neuroendocrine tumours.
11. Patients with known or suspected leptomeningeal metastases.
12. Uncontrolled or poorly controlled hypertension.
13. Patients with poorly controlled diabetes mellitus. Patients with a history of diabetes are allowed to participate, provided that their blood glucose is within normal range (fasting <160 mg/dL or below ULN) and that they are on a stable dietary or therapeutic regimen for this condition.
14. Known human immunodeficiency virus infection or acquired immunodeficiency syndrome-related illness.
15. Patients with epilepsy, seizures, or predisposing factors for seizure as judged by the investigator.
16. Patients unable to comply with the protocol as judged by the investigator.
17. Active alcohol or active drug abuse as judged by the investigator.
18. A history of allergy to human monoclonal antibodies.
19. Prior therapy with agents targeting IGF and/or IGFR pathway.
20. Patients who are sexually active and unwilling to use a medically acceptable method of contraception (e.g. such as implants, injectables, combined oral contraceptives, some intrauterine devices or vasectomized partner for participating females, condoms for participating males) during the trial and for at least three months after end of active therapy. Men unwilling to agree to not donate sperm while on trial drug and up to 6 months following the last dose of trial drug. Additional exclusion criteria for part II:
21. For patients that are to undergo the optional tumour biopsy, a history of a hereditary bleeding disorder, or clinically relevant major bleeding event in the past 6 months, as judged by the investigator.

Treatments to be Administered
Substance: IGF mAb_1 Human Monoclonal Antibody
Pharmaceutical form: Liquid formulation
Source: Boehringer Ingelheim Pharma GmbH & Co. KG
Unit strength: 10 mg/ml of IGF mAb_1 supplied in 20 ml vials. Appropriate dose of IGF mAb_1 will be diluted in physiological sodium chloride solution (0.9%).
Duration of use: One hour at the start of each week (Day 1, 8, 15 and 22) of a 28 day cycle of treatment until disease progression or undue toxicities. Infusion duration may be extended to over one hour in case of infusion reaction or adverse events.
Route of administration: Intravenous
Starting dose: 750 mg (up to 1000 mg) total dose by one hour i.v. infusion
Additional information: Dose will be adjusted during part I tolerability/safety and dose finding phase
Substance: Enzalutamide (Xtandi®)
Pharmaceutical form: Liquid-filled soft gelatin capsule
Source: Astellas
Unit strength: 40 mg
Duration of use: 160 mg once daily during each cycle of treatment
Route of administration: Oral
Starting dose: 160 mg once daily
Additional information: Dose will be adjusted during part I tolerability/safety and dose finding phase from that stated in the summary of product characteristics (SPC).

Table 1 gives an overview of the mutations, protein expression and effects of androgen and IGF signaling inhibition observed in the 15 different tested prostate cancer cell lines.

TABLE 1

| cell line | AR (protein) | IGF-1R (protein) | PTEN (protein) | PI3K (DNA) | TMPRSS2 fusion | Effect of AR signaling inhibition | Effect of IGF signaling inhibition | Effect of AR/IGF signaling inhibition combination | comments |
|---|---|---|---|---|---|---|---|---|---|
| 22Rv1 | + | ~ | + | mut (Q546R) | − | + | ~ | ~ | |
| BM-1604 | − | + | ~ | wt | − | − | ~ | ~ | derived from DU-145 |
| Bob | − | ~ | ~ | mut (I391H) | − | − | − | − | Spontaneously immortalized CRPC |
| C 4-2 | + | + | − | wt | − | + | − | − | LNCaP derived cell lines (xenograft in castrated mice) |
| C4-2B | + | + | − | wt | − | + | − | − | |
| DU 145 | − | + | − | wt | − | − | ~ | − | |
| * DUCaP | + | + | + | wt | ERG | + | + | +++ | Isolated from different metastases from some PCa patient as VCaP |
| LNCap.FGC | + | + | − | wt | − | + | − | − | |
| * MDA PCa 2b | + | + | + | wt | − | + | + | ++ | |
| NCI-H660 | − | ~ | − | n.d. | ERG | − | n.d. | n.d. | |
| P4E6 | − | + | ~ | wt | − | − | − | − | |
| PC-3 | − | + | − | wt | − | − | − | − | |
| Shmac4 | − | + | ~ | wt | − | − | − | − | |
| Shmac5 | − | + | ~ | wt | − | − | − | − | |
| * VCaP | + | + | + | wt | ERG | + | + | +++ | Isolated from different metastases from same PCa patient as DUCaP |

Cell lines labeled with an asterisk represent responsive cell lines expressing wt AR, wt PI3K, PTEN and IGF-1R.
Abbreviations:
AR = androgen receptor;
IGF-1R = Insulin-like growth factor 1 receptor;
mut = mutated;
n.d. = not determined;
wt = wild type

The invention claimed is:

1. A method of treatment of castration resistant prostate cancer comprising administering a therapeutically effective amount of an antibody comprising a heavy chain of SEQ ID NO: 39 and a light chain of SEQ ID NO: 40 which binds to IGF ligands IGF-1 and IGF-2 and reduces or blocks binding of IGF ligands IGF-1 and IGF-2 to their receptor in a patient in need thereof, and additionally administering a therapeutically effective amount of enzalutamide in combination with the antibody.

2. The method of claim 1, wherein the enzalutamide is administered to the patient within seven days before or after administration of the antibody.

* * * * *